United States Patent
Izumimoto et al.

(10) Patent No.: US 7,718,664 B2
(45) Date of Patent: May 18, 2010

(54) ANTI-ITCHING AGENT

(75) Inventors: Naoki Izumimoto, Kamakura (JP); Toshikazu Komagata, Kamakura (JP); Toshiyuki Honda, Hiratsuka (JP); Koji Kawai, Naka-gun (JP)

(73) Assignee: Toray Industries, Inc. (JP)

( * ) Notice: Subject to any disclaimer, the term of this patent is extended or adjusted under 35 U.S.C. 154(b) by 487 days.

(21) Appl. No.: 11/547,441

(22) PCT Filed: Mar. 30, 2005

(86) PCT No.: PCT/JP2005/006015

§ 371 (c)(1),
(2), (4) Date: Sep. 29, 2006

(87) PCT Pub. No.: WO2005/094826

PCT Pub. Date: Oct. 13, 2005

(65) Prior Publication Data
US 2008/0275074 A1    Nov. 6, 2008

(30) Foreign Application Priority Data
Mar. 30, 2004    (JP)    ................ 2004-097798

(51) Int. Cl.
A01N 43/42    (2006.01)
A61K 31/44    (2006.01)
(52) U.S. Cl. .................................. 514/282
(58) Field of Classification Search .............. 514/282
See application file for complete search history.

(56) References Cited

U.S. PATENT DOCUMENTS

| | | | |
|---|---|---|---|
| 3,318,884 A | | 5/1967 | Brown et al. |
| 5,760,023 A | * | 6/1998 | Farrar et al. ............... 514/150 |
| 5,869,521 A | | 2/1999 | Farrar et al. |
| 6,004,964 A | * | 12/1999 | Farrar et al. ............. 514/252.13 |
| 6,048,860 A | * | 4/2000 | Farrar et al. ............. 514/254.01 |
| 6,156,769 A | * | 12/2000 | Farrar et al. ............... 514/320 |

FOREIGN PATENT DOCUMENTS

| | | |
|---|---|---|
| JP | 41-6905 | 4/1941 |
| JP | 41-7786 | 4/1941 |
| JP | 41-18823 | 10/1941 |
| JP | 41-18824 | 10/1941 |
| JP | 41-18826 | 10/1941 |
| JP | 41-018823 B | 10/1964 |
| JP | 41-006905 B4 | 4/1966 |
| JP | 41-007786 B4 | 4/1966 |
| JP | 2002-308769 A | 10/2002 |
| JP | 2003-526594 A | 9/2003 |
| WO | WO 98/23290 A1 | 6/1998 |
| WO | 99/03459 A | 1/1999 |
| WO | 2004/033457 A1 | 4/2004 |
| WO | WO 2004/033457 A1 | 4/2004 |

OTHER PUBLICATIONS

Inan S and Cowan A, "Nalfurafine, a kappa opioid receptor agonist, inhibits scratching behavior secondary to cholestasis induced by chronic ethynylestradiol injections in rats," Pharmacology Biochemistry and Behavior, Sep. 2006, 85(1), 39-43.*

Metzger TG, Paterlini MG, Portoghese PS, and Ferguson DM, "Application of the message-address concept to the docking of naltrexone and selective naltrexone-derived opioid antagonists into opioid receptor models," Neurochemical Research, Nov. 1996, 21(11), 1287-1294.*

Nagase H, Hayakawa J, Kawamura K, Kawai K, Takezawa Y, Matsuura H, Tajima C, and Endo T, "Discovery of a structurally novel opioid kappa-agonist derived from 4,5-epoxymorphinan," Chemical & Pharmaceutical Bulletin, Feb. 1998, 46(2), 366-369.*

Togashi Y, Umeuchi H, Okano K, Ando N, Yoshizawa Y, Honda T, Kawamura K, Endoh T, Utsumi J, Kamei J, Tanaka T, and Nagase H, "Antipruritic activity of the kappa-opioid receptor agonist, TRK-820," European Journal of Pharmacology, Jan. 2002, 435(2-3), 259-264.*

Umeuchi H, Togashi Y, Honda T, Nakao K, Okano K, Tanaka T, and Nagase H, "Involvement of central mu-opioid system in the scratching behavior in mice, and the suppression of it by the activation of kappa-opioid system," European Journal of Pharmacology, Sep. 2003, 477(1), 29-35.*

(Continued)

Primary Examiner—San-ming Hui
Assistant Examiner—Paul Zarek
(74) Attorney, Agent, or Firm—DLA Piper LLP (US)

(57) ABSTRACT

A method of inhibiting or reducing occurrence or intensity of pruritus including administering to a patient an effective amount of one or more of the morphinan derivative having a nitrogen-containing cyclic group of the Formula (Ia):

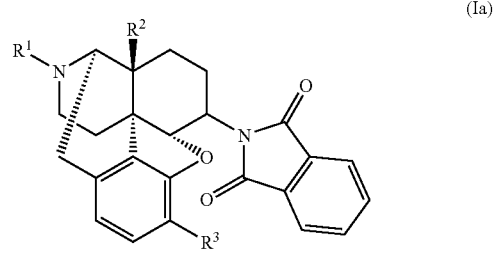

(Ia)

wherein $R^1$ is cyclopropylmethyl; $R^2$ and $R^3$ are independently hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy; and the Formula (Ia) includes (+), (−) and (±) isomers or the pharmaceutically acceptable acid addition salt thereof.

2 Claims, No Drawings

OTHER PUBLICATIONS

Joel E. Bernstein, M.D., et al., "Antipruritic Effect of an Opiate Antagonist, Naloxone Hydrochloride," The Journal of Investigative Dermatology, vol. 78, No. 1, Jan. 1982, pp. 82-83.

L.M. Sayre et al., "Design and Synthesis of Naltrexone-Derived Affinity Labels with Nonequilibrium Opioid Agonist and Antagonist Activities. Evidence for the Existence of Different μ Receptor Subtypes in Different Tissues," Journal of Medicinal Chemistry, vol. 27, No. 10, 1984, pp. 1325-1335.

Jerome H. Jaffe et al., "Opioid Analgesics and Antagonists," Goodman and Gilman's The Pharmacological Basis of Therapeutics, 1985.

J.R. Thornton et al., "Opioid Peptides and Primary Biliary Cirrhosis," Br. Med. J., vol. 297, Dec. 10, 1988, pp. 1501-1504.

Csaba Simon et al., "Application of the Mitstmobu Reaction for Morphine Compounds. Preparation of 6β-Aminomorphine and Codeine Derivatives," Synthetic Communications, vol. 22, No. 6, 1992, pp. 913-921.

Csaba Simon et al., "Stereoselective Synthesis of β-Naltrexol, β-Naloxol, β-Naloxamine, β-Naltrexamine and Related Compounds by the Application of the Mitsunobu Reaction," Tetrahedron, vol. 50, No. 32, 1994, pp. 9757-9768.

L. M. Sayre et al., *Design and Synthesis of Naltrexone-Derived Affinity Labels with Nonequilibrium Opioid Agonist and Antagonist Activities. Evidence for the Existence of Different μ Receptor Subtypes in Different Tissues*, J. Med. Chem. (1984), vol. 27, pp. 1325-1335.

* cited by examiner

ANTI-ITCHING AGENT

RELATED APPLICATION

This is a §371 of International Application No. PCT/JP2005/006015, with an international filing date of Mar. 30, 2005 (WO 2005/094826 A1, published Oct. 13, 2005), which is based on Japanese Patent Application No. 2004-097798, filed Mar. 30, 2004.

TECHNICAL FIELD

This disclosure relates to anantipruritic useful for the treatment of pruritus accompanying various diseases, comprising as an effective ingredient a morphin and derivative having a nitrogen-containing cyclic group or a pharmaceutically acceptable acid addition salt thereof.

BACKGROUND

Pruritus (itching) occurs in a variety of dermatoses with inflammation. It is known that pruritus is also sensed in internal diseases, pregnancy and vermination, and the pruritus is sometimes induced by drugs and by psychogenic reasons. Since quantitative and objective evaluation of pruritus is difficult, the study thereof has not been advanced, and the mechanism that induces pruritus has not yet been completely clarified. Reported substances which induce pruritus include histamine, substance P, bradykinin, proteinases, prostaglandins and opioid peptides.

For the treatment of pruritus, antihistamines and antiallergic drugs, which are oral drugs, have been mainly employed. External preparations such as antihistamines, adrenocortical steroid dermatologic preparations, nonsteroidal anti-inflammatory drugs, camphor, menthol, phenol, salicylic acid, tar, crotamiton, capsaicin, and humectants (urea, Hirudoid, and vaseline) have also been used. However, oral drugs have some problems, e.g. a long lag time before presenting effects, and adverse events such as suppressive effects on the central nervous system (drowsiness and malaise) and impairment of the gastrointestinal system. External preparations also have problems in that the antipruritic effect is insufficient, and especially, administration of steroid drugs for an extended period of time brings about systemic side effects such as decreased adrenal function as well as topical side effects such as rebound phenomenon, skin atrophy, steroid purpura, striae cutis distensae and steroid acne.

As for the findings concerning the relationship between the compounds having morphinan skeleton and pruritus, it has been reported that pruritus was induced when morphine was epidurally or intrathecally administered, opposite to the cases where the compounds used in the present invention are administered (J. H. Jaffe and W. R. Martin. Goodman and Gilman's Pharmacological Basis of Therapeutics, Macmillan, N.Y., 1985). On the other hand, it has been also reported the pruritus induced by intrathecally-administered morphine was suppressed by naloxone, an opioid antagonist (J. Bernstein et al. J. Invest. Dermatol., 78, 82-83, 1982), and severe pruritus in cases of cholestasia with hepathopathy was suppressed by nalmefene, an opioid antagonist (J. R. Thornton and M. S. Losowsky. Dr. Med. J., 297, 1501-1504, 1988). Further, morphinan compounds of which 6-position is substituted by a chain group, represented by the following general formula, which have antipruritic actions are also known (PCT International Publication WO 98/23290):

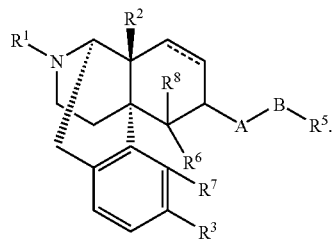

On the other hand, morphinan compounds having a nitrogen-containing cyclic group are known, which are described in J. Bernstein et al. J. Invest. Dermatol., 78, 82-83, 1982 and J. R. Thornton and M. S. Losowsky, Br. Med. J., 297, 1501-1504, 1988. The disclosed uses of the compounds are analgesic and antitussive only (J. Bernstein et al., J. Invest. Dermatol., 78, 82-83, 1982 and J. R. Thornton and M. S. Losowsky, Br. Med. J., 297, 1501-1504, 1988). In G. Simon et al. Tetrahedron. 50, 9757-9768, 1994, C. Simon et al., Synth. Commun. 22, 913-921, 1992 and L. M. Sayre et al., J. Med. Chem., 27, 1325-1335, 1984, only the compounds are described and no use thereof is disclosed (G. Simon et al., Tetrahedron, 50, 9757-9768, 1994, C. Simon et al. Synth. Commun. 22, 913-921, 1992 and L. M. Sayre et al., J. Med. Chem. 27, 1325-1335, 1984) (Use for the treatment of urinary frequency or urinary incontinence was disclosed after the priority date of this application (PCT international Publication WO 04/33457)). However, there is no constant relationship between the structures of these compounds as well as the pharmacological activities through opioid receptors and the like and the antipruritic action according to the present invention, so that the references do not infer the prominent and useful antipruritic action of the antipruritic according to the present invention characterized in that the morphinan structure has a nitrogen-containing cyclic group at its 6-position.

It could therefore be helpful to provide novel antipruritic useful for the therapy of pruritus accompanying various diseases.

SUMMARY

We discovered that compounds having a nitrogen-containing cyclic group on a specific position of morphinan structure have excellent therapeutic effects against pruritus and that their side effects are small.

We provide methods of treating the incidence of pruritus with the antipruritic comprising as an effective ingredient a morphinan derivative having a nitrogen-containing cyclic group of the Formula (I):

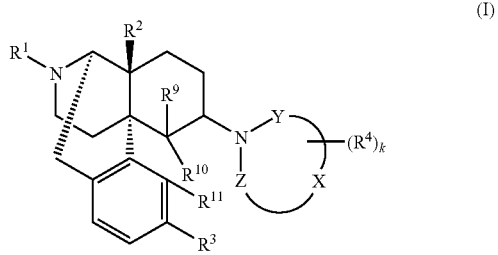

[wherein $R^1$ is hydrogen, $C_1$-$C_5$ alkyl, $C_4$-$C_7$ cycloalkylalkyl, $C_6$-$C_8$ cycloalkenylalkyl, $C_6$-$C_{12}$ aryl, $C_7$-$C_{13}$ aralkyl, $C_3$-$C_7$ alkenyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5);

$R^2$ and $R^3$ are independently hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy;

Y and Z independently represent valence bond or —C(=O)—;

—X— represents a $C_2$-$C_7$ carbon chain (one or more of the carbon atoms therein may be replaced by (a) nitrogen, oxygen or sulfur atom(s), and the carbon chain may contain (an) unsaturated bond(s)) constituting a part of the ring structure;

k is an integer of 0 to 8;

$R^4$ is(are) (a) substituent(s) in the number of k on the nitrogen-containing ring, which independently represent(s) fluorine, chlorine, bromine, iodine, nitro, hydroxy, $C_1$-$C_5$ alkyl, $C_7$-$C_{13}$ cycloalkylalkyl, $C_6$-$C_{12}$ aryl, $C_7$-$C_{13}$ aralkyl, $C_7$-$C_{13}$ aralkyloxy, $C_1$-$C_5$ alkoxy, trifluoromethyl, trifluoromethoxy, cyano, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$, or among the $R^4$s in the number of k, two $R^4$s bound to the same carbon atom or to the same sulfur atom cooperatively represent one oxygen atom to form carbonyl or sulfoxide, or two $R^4$s bound to the same carbon atom cooperatively represent one sulfur atom to form thiocarbonyl, or four $R^4$s bound to the same sulfur atom cooperatively represent two oxygen atoms to form sulfone, or among the $R^4$s in the number of k, two $R^4$s bound to adjacent carbon atoms, respectively, cooperatively form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of said fused rings is non-substituted or substituted by 1 or more $R^5$s, wherein $R^5$(s) independently represent(s) fluorine, chlorine, bromine, iodine, nitro, hydroxy, $C_1$-$C_5$ alkyl, $C_1$-$C_5$ alkoxy, trifluoromethyl, trifluoromethoxy, cyano, $C_6$-$C_{12}$ aryl, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$;

$R^9$ is hydrogen, $C_1$-$C_5$ alkyl, $C_1$-$C_5$ alkenyl, $C_7$-$C_{13}$ aralkyl, $C_1$-$C_3$ hydroxyalkyl, $(CH_2)_pOR^6$ or $(CH_2)_pCO_2R^6$;

$R^{10}$ and $R^{11}$ are bound to form —O—, —S— or —CH$_2$—, or $R^{10}$ is hydrogen and $R^{11}$ is hydrogen, hydroxy, $C_1$-$C_5$ alkoxy or $C_1$-$C_5$ alkanoyloxy;

p is an integer of 0 to 5;

$R^6$ is hydrogen, $C_1$-$C_5$ alkyl, $C_3$-$C_7$ alkenyl, $C_6$-$C_{12}$ aryl or $C_7$-$C_{13}$ aralkyl; and $R^7$ and $R^8$ are independently hydrogen, $C_1$-$C_5$ alkyl or $C_7$-$C_{13}$ aralkyl, and the Formula (I) includes (+), (−) and (±) isomers] or a pharmaceutically acceptable acid addition salt thereof.

We also provide a use of the morphinan derivative having a nitrogen-containing cyclic group, represented by the above-described Formula (I) or a pharmaceutically acceptable acid addition salt thereof for the production of antipruritics. We further provide a method for preventing pruritus comprising administering to a patient an effective amount of one or more of said morphinan derivative having a nitrogen-containing cyclic group, represented by the above-described Formula (I) or the pharmaceutically acceptable acid addition salt thereof.

DETAILED DESCRIPTION

The antipruritic has an excellent antipruritic property and its side effects are mall.

As mentioned above, the antipruritic comprises as an effective ingredient a morphinan derivative having a nitrogen-containing cyclic group of the Formula (I) or a pharmaceutically acceptable acid addition salt thereof. The antipruritic may comprise a single effective ingredient selected from the group consisting of the morphinan derivatives having a nitrogen-containing cyclic group of the Formula (I) and pharmaceutically acceptable acid addition salts thereof, or may comprise combination of two or more of the effective ingredients.

Among the compounds represented by Formula (I), those in which Y is —C(=O)— are preferred, and those in which both Y and Z are —C(=O)— are especially preferred.

$R^1$ is preferably hydrogen, $C_4$-$C_7$ cycloalkylalkyl, $C_6$-$C_8$ cycloalkenylalkyl, $C_6$-$C_{12}$ aryl or $C_3$-$C_7$ alkenyl. Among these, hydrogen, cyclopropylmethyl, 2-cyclopropylethyl, 3-cyclopropylpropyl, 4-cyclopropylbutyl, cyclobutylmethyl, cyclopentylmethyl, cyclohexylmethyl, cyclobutenylmethyl, 2-cyclobutenylethyl, 3-cyclobutenylpropyl, phenyl, naphthyl, tolyl, allyl, 3-butynyl and prenyl are preferred. Among these, hydrogen, cyclopropylmethyl, cyclobutylmethyl, cyclopentylmethyl, cyclohexylmethyl, allyl and prenyl are preferred, and hydrogen, cyclopropylmethyl, cyclobutylmethyl and allyl are especially preferred.

$R^2$ and $R^3$ are hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy. Among these, hydrogen, hydroxy, methoxy, ethoxy, allyloxy, benzyloxy, acetoxy and propionoxy are preferred, and hydrogen, hydroxy, methoxy and acetoxy are especially preferred.

—X— is preferably a $C_2$-$C_4$ carbon chain (one carbon atom therein may be replaced by sulfur atom and the carbon chain contains (an) unsaturated bond(s)) constituting a part of the ring structure, and more preferably a carbon chain having two carbon atoms, constituting a part of the ring structure.

k is preferably an integer of 0 to 6.

$R^4$(s) is(are) preferably $C_1$-$C_5$ alkyl, $C_7$-$C_{13}$ aralkyl or $C_7$-$C_{13}$ aralkyloxy, or preferably, four $R^4$s bound to the same sulfur atom cooperatively represent two oxygen atoms to form sulfone, or preferably, two $R^4$s bound to adjacent carbon atoms, respectively, cooperatively form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of said fused rings is non-substituted or substituted by 1 or more $R^5$s. Among these, methyl, ethyl, ethylidene, propyl, propylidene, butyl, butylidene, benzyl, benzylidene, methylbenzyl, methylbenzylidene, fluorobenzyl, fluorobenzylidene, trifluoromethoxybenzyl, trifluoromethoxybenzylidene, phenethyl, phenethylidene, cyclohexylmethyl, cyclohexylmethylidene, phenoxy and chlorophenoxy, as well as formation of sulfone group, or benzene fused ring and cyclohexene fused ring, are preferred. Especially preferred are the cases where two $R^4$s cooperatively form benzene fused ring or cyclohexene fused ring, each of which is non-substituted or substituted by 1 to 4 substituent $R^5$s. In these cases, the cases where additional four $R^4$s bound to the same sulfur atom cooperatively form a sulfone group are also preferred. Although formation of non-substituted benzene fused ring or non-substituted cyclohexene fused ring is preferred, the cases are also preferred where $R^5$(s) is(are) independently fluorine, chlorine, bromine, iodine, nitro, $C_1$-$C_5$ alkyl (especially, methyl, ethyl or propyl), $C_7$-$C_{13}$ aralkyl (especially benzyl), hydroxy, $C_1$-$C_5$ alkoxy (especially methoxy or ethoxy), trifluoromethyl, trifluoromethoxy, cyano, phenyl, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$, $(CH_2)_pN(R^7)COR^8$ (wherein p represents an integer of 0 to 5, $R^6$ represents hydrogen, $C_1$-$C_5$ alkyl (especially methyl, ethyl or propyl), $C_3$-$C_7$ alkenyl or $C_6$-$C_{12}$ aryl (especially phenyl), and $R^7$ and $R^8$ independently represent hydrogen, $C_1$-$C_5$ alkyl (especially methyl, ethyl or propyl) or $C_7$-$C_{13}$ aralkyl (especially benzyl)). Especially preferred are cases where the fused ring is non-substituted and the cases where $R^5$(s) is(are) fluorine, chlorine, bromine, iodine, nitro, methyl, ethyl, propyl, benzyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, acetoxy, phenyloxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl or amino.

$R^9$ is preferably hydrogen, $C_1$-$C_5$ alkyl, allyl or benzyl, and more preferably hydrogen or methyl.

As for $R^{10}$ and $R^{11}$, preferred are the cases where $R^{10}$ and $R^{11}$ are bound to form —O—, or $R^{10}$ is hydrogen and $R^{11}$ is hydrogen, hydroxy or methoxy, and the cases where $R^{10}$ and $R^{11}$ are bound to form —O— are especially preferred.

Preferred examples of the pharmaceutically acceptable acid addition salts include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid salt and the like are preferred, but the acid addition salt is not restricted thereto.

Among the compounds of the Formula (I), specific examples of those wherein —X— is a carbon chain having two carbon atoms constituting a part of the ring structure; Y and Z are —C(═O)—; two $R^4$s form benzene fused ring which is not substituted or substituted by one or more $R^5$s; $R^9$ hydrogen; $R^{10}$ and $R^{11}$ are bound to represent —O—, that is, those represented by the Formula (Ia) below are shown in Table 1. In the tables described below, CPM means cyclopropylmethyl, and the bond at 6-position is α or β.

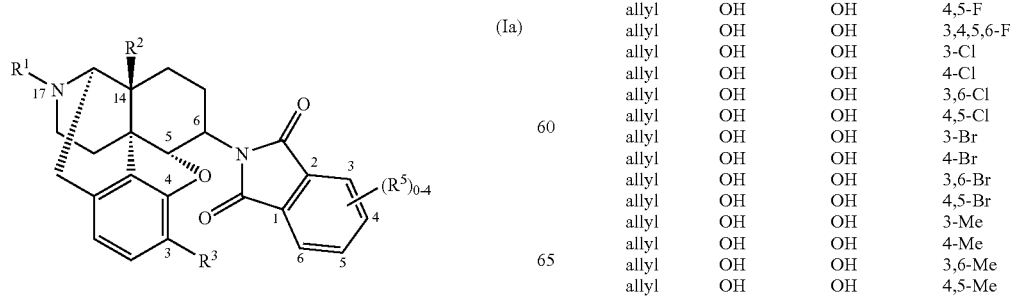

(Ia)

Among the compounds represented by Formula (Ia), the compound wherein $R^1$ is cyclopropylmethyl, $R^2$ and $R^3$ are hydroxy, $R^5$ is 4-fluoro, and the configuration of the bond at the 6-position is β, that is, the compound of the following formula:

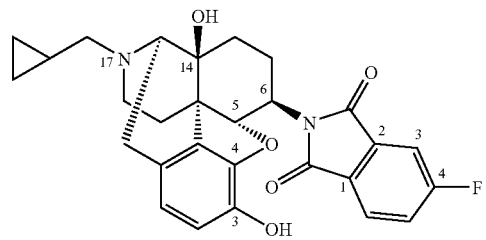

is named N-[17-(cyclopropylmethyl)-4,5α-epoxy-3,14-dihydroxymorphinan-6β-yl]-4-fluorophthalimide.

TABLE 1

| $R^1$ | $R^2$ | $R^3$ | $R^5$ |
|---|---|---|---|
| CPM | OH | OH | (non-substituted) |
| CPM | OH | OH | 3-F |
| CPM | OH | OH | 4-F |
| CPM | OH | OH | 3,6-F |
| CPM | OH | OH | 4,5-F |
| CPM | OH | OH | 3,4,5,6-F |
| CPM | OH | OH | 3-Cl |
| CPM | OH | OH | 4-Cl |
| CPM | OH | OH | 3,6-Cl |
| CPM | OH | OH | 4,5-Cl |
| CPM | OH | OH | 3-Br |
| CPM | OH | OH | 4-Br |
| CPM | OH | OH | 3,6-Br |
| CPM | OH | OH | 4,5-Br |
| CPM | OH | OH | 3-Me |
| CPM | OH | OH | 4-Me |
| CPM | OH | OH | 3,6-Me |
| CPM | OH | OH | 4,5-Me |
| CPM | OH | OH | 3-OMe |
| CPM | OH | OH | 4-OMe |
| CPM | OH | OH | 3,6-OMe |
| CPM | OH | OH | 4,5-OMe |
| CPM | OH | OH | 3-OH |
| CPM | OH | OH | 4-OH |
| CPM | OH | OH | 3,6-OH |
| CPM | OH | OH | 4,5-OH |
| CPM | OH | OH | 3-$NO_2$ |
| CPM | OH | OH | 4-$NO_2$ |
| CPM | OH | OH | 3,6-$NO_2$ |
| CPM | OH | OH | 4,5-$NO_2$ |
| CPM | OH | OH | 3-$NH_2$ |
| CPM | OH | OH | 4-$NH_2$ |
| CPM | OH | OH | 3,6-$NH_2$ |
| CPM | OH | OH | 4,5-$NH_2$ |
| allyl | OH | OH | (non-substituted) |
| allyl | OH | OH | 3-F |
| allyl | OH | OH | 4-F |
| allyl | OH | OH | 3,6-F |
| allyl | OH | OH | 4,5-F |
| allyl | OH | OH | 3,4,5,6-F |
| allyl | OH | OH | 3-Cl |
| allyl | OH | OH | 4-Cl |
| allyl | OH | OH | 3,6-Cl |
| allyl | OH | OH | 4,5-Cl |
| allyl | OH | OH | 3-Br |
| allyl | OH | OH | 4-Br |
| allyl | OH | OH | 3,6-Br |
| allyl | OH | OH | 4,5-Br |
| allyl | OH | OH | 3-Me |
| allyl | OH | OH | 4-Me |
| allyl | OH | OH | 3,6-Me |
| allyl | OH | OH | 4,5-Me |

TABLE 1-continued

| R¹ | R² | R³ | R⁵ |
|---|---|---|---|
| allyl | OH | OH | 3-OMe |
| allyl | OH | OH | 4-OMe |
| allyl | OH | OH | 3,6-OMe |
| allyl | OH | OH | 4,5-OMe |
| allyl | OH | OH | 3-OH |
| allyl | OH | OH | 4-OH |
| allyl | OH | OH | 3,6-OH |
| allyl | OH | OH | 4,5-OH |
| allyl | OH | OH | 3-NO₂ |
| allyl | OH | OH | 4-NO₂ |
| allyl | OH | OH | 3,6-NO₂ |
| allyl | OH | OH | 4,5-NO₂ |
| allyl | OH | OH | 3-NH₂ |
| allyl | OH | OH | 4-NH₂ |
| allyl | OH | OH | 3,6-NH₂ |
| allyl | OH | OH | 4,5-NH₂ |
| CPM | H | OH | (non-substituted) |
| CPM | H | OH | 3-F |
| CPM | H | OH | 4-F |
| CPM | H | OH | 3,6-F |
| CPM | H | OH | 4,5-F |
| CPM | H | OH | 3,4,5,6-F |
| CPM | H | OH | 3-Cl |
| CPM | H | OH | 4-Cl |
| CPM | H | OH | 3,6-Cl |
| CPM | H | OH | 4,5-Cl |
| CPM | H | OH | 3-Br |
| CPM | H | OH | 4-Br |
| CPM | H | OH | 3,6-Br |
| CPM | H | OH | 4,5-Br |
| CPM | H | OH | 3-Me |
| CPM | H | OH | 4-Me |
| CPM | H | OH | 3,6-Me |
| CPM | H | OH | 4,5-Me |
| CPM | H | OH | 3-OMe |
| CPM | H | OH | 4-OMe |
| CPM | H | OH | 3,6-OMe |
| CPM | H | OH | 4,5-OMe |
| CPM | H | OH | 3-OH |
| CPM | H | OH | 4-OH |
| CPM | H | OH | 3,6-OH |
| CPM | H | OH | 4,5-OH |
| CPM | H | OH | 3-NO₂ |
| CPM | H | OH | 4-NO₂ |
| CPM | H | OH | 3,6-NO₂ |
| CPM | H | OH | 4,5-NO₂ |
| CPM | H | OH | 3-NH₂ |
| CPM | H | OH | 4-NH₂ |
| CPM | H | OH | 3,6-NH₂ |
| CPM | H | OH | 4,5-NH₂ |
| allyl | H | OH | (non-substituted) |
| allyl | H | OH | 3-F |
| allyl | H | OH | 4-F |
| allyl | H | OH | 3,6-F |
| allyl | H | OH | 4,5-F |
| allyl | H | OH | 3,4,5,6-F |
| allyl | H | OH | 3-Cl |
| allyl | H | OH | 4-Cl |
| allyl | H | OH | 3,6-Cl |
| allyl | H | OH | 4,5-Cl |
| allyl | H | OH | 3-Br |
| allyl | H | OH | 4-Br |
| allyl | H | OH | 3,6-Br |
| allyl | H | OH | 4,5-Br |
| allyl | H | OH | 3-Me |
| allyl | H | OH | 4-Me |
| allyl | H | OH | 3,6-Me |
| allyl | H | OH | 4,5-Me |
| allyl | H | OH | 3-OMe |
| allyl | H | OH | 4-OMe |
| allyl | H | OH | 3,6-OMe |
| allyl | H | OH | 4,5-OMe |
| allyl | H | OH | 3-OH |
| allyl | H | OH | 4-OH |
| allyl | H | OH | 3,6-OH |
| allyl | H | OH | 4,5-OH |
| allyl | H | OH | 3-NO₂ |
| allyl | H | OH | 4-NO₂ |
| allyl | H | OH | 3,6-NO₂ |
| allyl | H | OH | 4,5-NO₂ |
| allyl | H | OH | 3-NH₂ |
| allyl | H | OH | 4-NH₂ |
| allyl | H | OH | 3,6-NH₂ |
| allyl | H | OH | 4,5-NH₂ |
| CPM | OAc | OH | (non-substituted) |
| CPM | OAc | OH | 3-F |
| CPM | OAc | OH | 4-F |
| CPM | OAc | OH | 3,6-F |
| CPM | OAc | OH | 4,5-F |
| CPM | OAc | OH | 3,4,5,6-F |
| CPM | OAc | OH | 3-Cl |
| CPM | OAc | OH | 4-Cl |
| CPM | OAc | OH | 3,6-Cl |
| CPM | OAc | OH | 4,5-Cl |
| CPM | OAc | OH | 3-Br |
| CPM | OAc | OH | 4-Br |
| CPM | OAc | OH | 3,6-Br |
| CPM | OAc | OH | 4,5-Br |
| CPM | OAc | OH | 3-Me |
| CPM | OAc | OH | 4-Me |
| CPM | OAc | OH | 3,6-Me |
| CPM | OAc | OH | 4,5-Me |
| CPM | OAc | OH | 3-OMe |
| CPM | OAc | OH | 4-OMe |
| CPM | OAc | OH | 3,6-OMe |
| CPM | OAc | OH | 4,5-OMe |
| CPM | OAc | OH | 3-OH |
| CPM | OAc | OH | 4-OH |
| CPM | OAc | OH | 3,6-OH |
| CPM | OAc | OH | 4,5-OH |
| CPM | OAc | OH | 3-NO₂ |
| CPM | OAc | OH | 4-NO₂ |
| CPM | OAc | OH | 3,6-NO₂ |
| CPM | OAc | OH | 4,5-NO₂ |
| CPM | OAc | OH | 3-NH₂ |
| CPM | OAc | OH | 4-NH₂ |
| CPM | OAc | OH | 3,6-NH₂ |
| CPM | OAc | OH | 4,5-NH₂ |
| allyl | OAc | OH | (non-substituted) |
| allyl | OAc | OH | 3-F |
| allyl | OAc | OH | 4-F |
| allyl | OAc | OH | 3,6-F |
| allyl | OAc | OH | 4,5-F |
| allyl | OAc | OH | 3,4,5,6-F |
| allyl | OAc | OH | 3-Cl |
| allyl | OAc | OH | 4-Cl |
| allyl | OAc | OH | 3,6-Cl |
| allyl | OAc | OH | 4,5-Cl |
| allyl | OAc | OH | 3-Br |
| allyl | OAc | OH | 4-Br |
| allyl | OAc | OH | 3,6-Br |
| allyl | OAc | OH | 4,5-Br |
| allyl | OAc | OH | 3-Me |
| allyl | OAc | OH | 4-Me |
| allyl | OAc | OH | 3,6-Me |
| allyl | OAc | OH | 4,5-Me |
| allyl | OAc | OH | 3-OMe |
| allyl | OAc | OH | 4-OMe |
| allyl | OAc | OH | 3,6-OMe |
| allyl | OAc | OH | 4,5-OMe |
| allyl | OAc | OH | 3-OH |
| allyl | OAc | OH | 4-OH |
| allyl | OAc | OH | 3,6-OH |
| allyl | OAc | OH | 4,5-OH |
| allyl | OAc | OH | 3-NO₂ |
| allyl | OAc | OH | 4-NO₂ |
| allyl | OAc | OH | 3,6-NO₂ |
| allyl | OAc | OH | 4,5-NO₂ |
| allyl | OAc | OH | 3-NH₂ |
| allyl | OAc | OH | 4-NH₂ |
| allyl | OAc | OH | 3,6-NH₂ |
| allyl | OAc | OH | 4,5-NH₂ |

Among the compounds of the Formula (I), specific examples of those wherein —X— is a carbon chain having three carbon atoms constituting a part of the ring structure; Y is —C(=O)— and Z is valence bond; two $R^4$s form benzene fused ring which is not substituted or substituted by one or more $R^5$s; $R^9$ is hydrogen; $R^{10}$ and $R^{11}$ are bound to represent —O—, that is, those represented by the Formula (Ib) below are shown in Table 2.

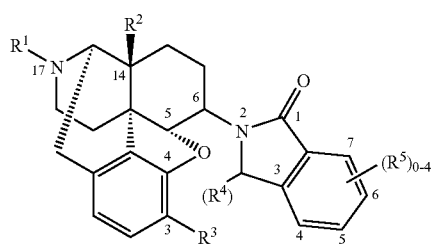
(Ib)

Among the compounds represented by Formula (Ib), the compound wherein $R^1$ is cyclopropylmethyl, $R^2$ and $R^3$ are hydroxy, $R^5$ is 6-fluoro, and the configuration of the bond at the 6-position is β, that is, the compound of the following formula:

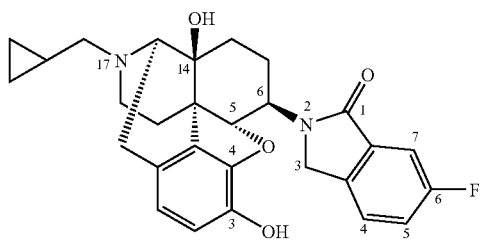

is named 2-[17-(cyclopropylmethyl)-4,5α-epoxy-3,14-dihydroxymorphinan-6β-yl]-6-fluoro-2,3-dihydro-isoindol-1-one.

TABLE 2

| $R^1$ | $R^2$ | $R^3$ | $R^4$ | $R^5$ |
|---|---|---|---|---|
| CPM | OH | OH | — | (non-substituted) |
| CPM | OH | OH | — | 4-F |
| CPM | OH | OH | — | 5-F |
| CPM | OH | OH | — | 6-F |
| CPM | OH | OH | — | 7-F |
| CPM | OH | OH | — | 5,6-F |
| CPM | OH | OH | — | 4,5,6,7-F |
| CPM | OH | OH | — | 4-Cl |
| CPM | OH | OH | — | 5-Cl |
| CPM | OH | OH | — | 6-Cl |
| CPM | OH | OH | — | 7-Cl |
| CPM | OH | OH | — | 5,6-Cl |
| CPM | OH | OH | — | 4-Me |
| CPM | OH | OH | — | 5-Me |
| CPM | OH | OH | — | 6-Me |
| CPM | OH | OH | — | 7-Me |
| CPM | OH | OH | — | 5,6-Me |
| CPM | OH | OH | — | 4-OMe |
| CPM | OH | OH | — | 5-OMe |
| CPM | OH | OH | — | 6-OMe |
| CPM | OH | OH | — | 7-OMe |
| CPM | OH | OH | — | 5,6-OMe |
| allyl | OH | OH | — | (non-substituted) |
| allyl | OH | OH | — | 4-F |
| allyl | OH | OH | — | 5-F |
| allyl | OH | OH | — | 6-F |
| allyl | OH | OH | — | 7-F |
| allyl | OH | OH | — | 5,6-F |
| allyl | OH | OH | — | 4,5,6,7-F |
| allyl | OH | OH | — | 4-Cl |
| allyl | OH | OH | — | 5-Cl |
| allyl | OH | OH | — | 6-Cl |
| allyl | OH | OH | — | 7-Cl |
| allyl | OH | OH | — | 5,6-Cl |
| allyl | OH | OH | — | 4-Me |
| allyl | OH | OH | — | 5-Me |
| allyl | OH | OH | — | 6-Me |
| allyl | OH | OH | — | 7-Me |
| allyl | OH | OH | — | 5,6-Me |
| allyl | OH | OH | — | 4-OMe |
| allyl | OH | OH | — | 5-OMe |
| allyl | OH | OH | — | 6-OMe |
| allyl | OH | OH | — | 7-OMe |
| allyl | OH | OH | — | 5,6-OMe |
| CPM | H | OH | — | (non-substituted) |
| CPM | H | OH | — | 4-F |
| CPM | H | OH | — | 5-F |
| CPM | H | OH | — | 6-F |
| CPM | H | OH | — | 7-F |
| CPM | H | OH | — | 5,6-F |
| CPM | H | OH | — | 4,5,6,7-F |
| CPM | H | OH | — | 4-Cl |
| CPM | H | OH | — | 5-Cl |
| CPM | H | OH | — | 6-Cl |
| CPM | H | OH | — | 7-Cl |
| CPM | H | OH | — | 5,6-Cl |
| CPM | H | OH | — | 4-Me |
| CPM | H | OH | — | 5-Me |
| CPM | H | OH | — | 6-Me |
| CPM | H | OH | — | 7-Me |
| CPM | H | OH | — | 5,6-Me |
| CPM | H | OH | — | 4-OMe |
| CPM | H | OH | — | 5-OMe |
| CPM | H | OH | — | 6-OMe |
| CPM | H | OH | — | 7-OMe |
| CPM | H | OH | — | 5,6-OMe |
| allyl | H | OH | — | (non-substituted) |
| allyl | H | OH | — | 4-F |
| allyl | H | OH | — | 5-F |
| allyl | H | OH | — | 6-F |
| allyl | H | OH | — | 7-F |
| allyl | H | OH | — | 5,6-F |
| allyl | H | OH | — | 4,5,6,7-F |
| allyl | H | OH | — | 4-Cl |
| allyl | H | OH | — | 5-Cl |
| allyl | H | OH | — | 6-Cl |
| allyl | H | OH | — | 7-Cl |
| allyl | H | OH | — | 5,6-Cl |
| allyl | H | OH | — | 4-Me |
| allyl | H | OH | — | 5-Me |
| allyl | H | OH | — | 6-Me |
| allyl | H | OH | — | 7-Me |
| allyl | H | OH | — | 5,6-Me |
| allyl | H | OH | — | 4-OMe |
| allyl | H | OH | — | 5-OMe |
| allyl | H | OH | — | 6-OMe |
| allyl | H | OH | — | 7-OMe |
| allyl | H | OH | — | 5,6-OMe |
| CPM | OH | OH | OH | (non-substituted) |
| CPM | OH | OH | OH | 4-F |
| CPM | OH | OH | OH | 5-F |
| CPM | OH | OH | OH | 6-F |
| CPM | OH | OH | OH | 7-F |
| CPM | OH | OH | OH | 5,6-F |
| CPM | OH | OH | OH | 4,5,6,7-F |
| CPM | OH | OH | OH | 4-Cl |
| CPM | OH | OH | OH | 5-Cl |
| CPM | OH | OH | OH | 6-Cl |
| CPM | OH | OH | OH | 7-Cl |
| CPM | OH | OH | OH | 5,6-Cl |
| CPM | OH | OH | OH | 4-Me |

TABLE 2-continued

| R¹ | R² | R³ | R⁴ | R⁵ |
|---|---|---|---|---|
| CPM | OH | OH | OH | 5-Me |
| CPM | OH | OH | OH | 6-Me |
| CPM | OH | OH | OH | 7-Me |
| CPM | OH | OH | OH | 5,6-Me |
| CPM | OH | OH | OH | 4-OMe |
| CPM | OH | OH | OH | 5-OMe |
| CPM | OH | OH | OH | 6-OMe |
| CPM | OH | OH | OH | 7-OMe |
| CPM | OH | OH | OH | 5,6-OMe |
| allyl | OH | OH | OH | (non-substituted) |
| allyl | OH | OH | OH | 4-F |
| allyl | OH | OH | OH | 5-F |
| allyl | OH | OH | OH | 6-F |
| allyl | OH | OH | OH | 7-F |
| allyl | OH | OH | OH | 5,6-F |
| allyl | OH | OH | OH | 4,5,6,7-F |
| allyl | OH | OH | OH | 4-Cl |
| allyl | OH | OH | OH | 5-Cl |
| allyl | OH | OH | OH | 6-Cl |
| allyl | OH | OH | OH | 7-Cl |
| allyl | OH | OH | OH | 5,6-Cl |
| allyl | OH | OH | OH | 4-Me |
| allyl | OH | OH | OH | 5-Me |
| allyl | OH | OH | OH | 6-Me |
| allyl | OH | OH | OH | 7-Me |
| allyl | OH | OH | OH | 5,6-Me |
| allyl | OH | OH | OH | 4-OMe |
| allyl | OH | OH | OH | 5-OMe |
| allyl | OH | OH | OH | 6-OMe |
| allyl | OH | OH | OH | 7-OMe |
| allyl | OH | OH | OH | 5,6-OMe |
| CPM | H | OH | OH | (non-substituted) |
| CPM | H | OH | OH | 4-F |
| CPM | H | OH | OH | 5-F |
| CPM | H | OH | OH | 6-F |
| CPM | H | OH | OH | 7-F |
| CPM | H | OH | OH | 5,6-F |
| CPM | H | OH | OH | 4,5,6,7-F |
| CPM | H | OH | OH | 4-Cl |
| CPM | H | OH | OH | 5-Cl |
| CPM | H | OH | OH | 6-Cl |
| CPM | H | OH | OH | 7-Cl |
| CPM | H | OH | OH | 5,6-Cl |
| CPM | H | OH | OH | 4-Me |
| CPM | H | OH | OH | 5-Me |
| CPM | H | OH | OH | 6-Me |
| CPM | H | OH | OH | 7-Me |
| CPM | H | OH | OH | 5,6-Me |
| CPM | H | OH | OH | 4-OMe |
| CPM | H | OH | OH | 5-OMe |
| CPM | H | OH | OH | 6-OMe |
| CPM | H | OH | OH | 7-OMe |
| CPM | H | OH | OH | 5,6-OMe |
| allyl | H | OH | OH | (non-substituted) |
| allyl | H | OH | OH | 4-F |
| allyl | H | OH | OH | 5-F |
| allyl | H | OH | OH | 6-F |
| allyl | H | OH | OH | 7-F |
| allyl | H | OH | OH | 5,6-F |
| allyl | H | OH | OH | 4,5,6,7-F |
| allyl | H | OH | OH | 4-Cl |
| allyl | H | OH | OH | 5-Cl |
| allyl | H | OH | OH | 6-Cl |
| allyl | H | OH | OH | 7-Cl |
| allyl | H | OH | OH | 5,6-Cl |
| allyl | H | OH | OH | 4-Me |
| allyl | H | OH | OH | 5-Me |
| allyl | H | OH | OH | 6-Me |
| allyl | H | OH | OH | 7-Me |
| allyl | H | OH | OH | 5,6-Me |
| allyl | H | OH | OH | 4-OMe |
| allyl | H | OH | OH | 5-OMe |
| allyl | H | OH | OH | 6-OMe |
| allyl | H | OH | OH | 7-OMe |
| allyl | H | OH | OH | 5,6-OMe |
| CPM | OH | OH | CH₂COOMe | (non-substituted) |
| CPM | OH | OH | CH₂COOMe | 4-F |
| CPM | OH | OH | CH₂COOMe | 5-F |
| CPM | OH | OH | CH₂COOMe | 6-F |
| CPM | OH | OH | CH₂COOMe | 7-F |
| CPM | OH | OH | CH₂COOMe | 5,6-F |
| CPM | OH | OH | CH₂COOMe | 4,5,6,7-F |
| CPM | OH | OH | CH₂COOMe | 4-Cl |
| CPM | OH | OH | CH₂COOMe | 5-Cl |
| CPM | OH | OH | CH₂COOMe | 6-Cl |
| CPM | OH | OH | CH₂COOMe | 7-Cl |
| CPM | OH | OH | CH₂COOMe | 5,6-Cl |
| CPM | OH | OH | CH₂COOMe | 4-Me |
| CPM | OH | OH | CH₂COOMe | 5-Me |
| CPM | OH | OH | CH₂COOMe | 6-Me |
| CPM | OH | OH | CH₂COOMe | 7-Me |
| CPM | OH | OH | CH₂COOMe | 5,6-Me |
| CPM | OH | OH | CH₂COOMe | 4-OMe |
| CPM | OH | OH | CH₂COOMe | 5-OMe |
| CPM | OH | OH | CH₂COOMe | 6-OMe |
| CPM | OH | OH | CH₂COOMe | 7-OMe |
| CPM | OH | OH | CH₂COOMe | 5,6-OMe |
| allyl | OH | OH | CH₂COOMe | (non-substituted) |
| allyl | OH | OH | CH₂COOMe | 4-F |
| allyl | OH | OH | CH₂COOMe | 5-F |
| allyl | OH | OH | CH₂COOMe | 6-F |
| allyl | OH | OH | CH₂COOMe | 7-F |
| allyl | OH | OH | CH₂COOMe | 5,6-F |
| allyl | OH | OH | CH₂COOMe | 4,5,6,7-F |
| allyl | OH | OH | CH₂COOMe | 4-Cl |
| allyl | OH | OH | CH₂COOMe | 5-Cl |
| allyl | OH | OH | CH₂COOMe | 6-Cl |
| allyl | OH | OH | CH₂COOMe | 7-Cl |
| allyl | OH | OH | CH₂COOMe | 5,6-Cl |
| allyl | OH | OH | CH₂COOMe | 4-Me |
| allyl | OH | OH | CH₂COOMe | 5-Me |
| allyl | OH | OH | CH₂COOMe | 6-Me |
| allyl | OH | OH | CH₂COOMe | 7-Me |
| allyl | OH | OH | CH₂COOMe | 5,6-Me |
| allyl | OH | OH | CH₂COOMe | 4-OMe |
| allyl | OH | OH | CH₂COOMe | 5-OMe |
| allyl | OH | OH | CH₂COOMe | 6-OMe |
| allyl | OH | OH | CH₂COOMe | 7-OMe |
| allyl | OH | OH | CH₂COOMe | 5,6-OMe |
| CPM | H | OH | CH₂COOMe | (non-substituted) |
| CPM | H | OH | CH₂COOMe | 4-F |
| CPM | H | OH | CH₂COOMe | 5-F |
| CPM | H | OH | CH₂COOMe | 6-F |
| CPM | H | OH | CH₂COOMe | 7-F |
| CPM | H | OH | CH₂COOMe | 5,6-F |
| CPM | H | OH | CH₂COOMe | 4,5,6,7-F |
| CPM | H | OH | CH₂COOMe | 4-Cl |
| CPM | H | OH | CH₂COOMe | 5-Cl |
| CPM | H | OH | CH₂COOMe | 6-Cl |
| CPM | H | OH | CH₂COOMe | 7-Cl |
| CPM | H | OH | CH₂COOMe | 5,6-Cl |
| CPM | H | OH | CH₂COOMe | 4-Me |
| CPM | H | OH | CH₂COOMe | 5-Me |
| CPM | H | OH | CH₂COOMe | 6-Me |
| CPM | H | OH | CH₂COOMe | 7-Me |
| CPM | H | OH | CH₂COOMe | 5,6-Me |
| CPM | H | OH | CH₂COOMe | 4-OMe |
| CPM | H | OH | CH₂COOMe | 5-OMe |
| CPM | H | OH | CH₂COOMe | 6-OMe |
| CPM | H | OH | CH₂COOMe | 7-OMe |
| CPM | H | OH | CH₂COOMe | 5,6-OMe |
| allyl | H | OH | CH₂COOMe | (non-substituted) |
| allyl | H | OH | CH₂COOMe | 4-F |
| allyl | H | OH | CH₂COOMe | 5-F |
| allyl | H | OH | CH₂COOMe | 6-F |
| allyl | H | OH | CH₂COOMe | 7-F |
| allyl | H | OH | CH₂COOMe | 5,6-F |
| allyl | H | OH | CH₂COOMe | 4,5,6,7-F |
| allyl | H | OH | CH₂COOMe | 4-Cl |
| allyl | H | OH | CH₂COOMe | 5-Cl |
| allyl | H | OH | CH₂COOMe | 6-Cl |
| allyl | H | OH | CH₂COOMe | 7-Cl |
| allyl | H | OH | CH₂COOMe | 5,6-Cl |
| allyl | H | OH | CH₂COOMe | 4-Me |

TABLE 2-continued

| R¹ | R² | R³ | R⁴ | R⁵ |
|---|---|---|---|---|
| allyl | H | OH | CH₂COOMe | 5-Me |
| allyl | H | OH | CH₂COOMe | 6-Me |
| allyl | H | OH | CH₂COOMe | 7-Me |
| allyl | H | OH | CH₂COOMe | 5,6-Me |
| allyl | H | OH | CH₂COOMe | 4-OMe |
| allyl | H | OH | CH₂COOMe | 5-OMe |
| allyl | H | OH | CH₂COOMe | 6-OMe |
| allyl | H | OH | CH₂COOMe | 7-OMe |
| allyl | H | OH | CH₂COOMe | 5,6-OMe |

Among the compounds represented by Formula (I), specific examples of the compound wherein —X— is a carbon chain having three carbon atoms (one of the carbon atoms is replaced by sulfur atom) constituting a part of the ring structure, Y is —C(=O), Z is valence bond, four R⁴s bound to the same sulfur atom cooperatively represent two oxygen atoms to form sulfone group, two R⁴s cooperatively form a benzene fused ring which is non-substituted or substituted by one or more R⁵s; R⁹ is hydrogen, R¹⁰ and R¹¹ are bound to form —O—, that is, the examples of the compounds represented by the following Formula (Ic) are shown in Table 3.

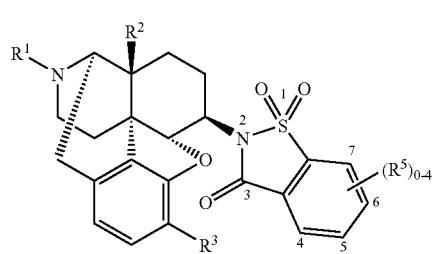

(Ic)

Among the compounds represented by Formula (Ic), the compound wherein R¹ is cyclopropylmethyl, R² and R³ are hydroxy, the benzene ring is not substituted, and the configuration of the bond at the 6-position is β, that is, the compound of the following formula:

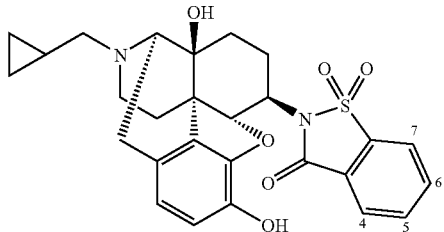

is named N-[17-(cyclopropylmethyl)-4,5α-epoxy-3,14-dihydroxymorphinan-6β-yl]-O-sulfonebenzimide.

TABLE 3

| R¹ | R² | R³ | R⁵ |
|---|---|---|---|
| CPM | OH | OH | (non-substituted) |
| CPM | OH | OH | 4-F |
| CPM | OH | OH | 5-F |
| CPM | OH | OH | 6-F |
| CPM | OH | OH | 7-F |

TABLE 3-continued

| R¹ | R² | R³ | R⁵ |
|---|---|---|---|
| CPM | OH | OH | 5,6-F |
| CPM | OH | OH | 4,5,6,7-F |
| CPM | OH | OH | 4-Cl |
| CPM | OH | OH | 5-Cl |
| CPM | OH | OH | 6-Cl |
| CPM | OH | OH | 7-Cl |
| CPM | OH | OH | 5,6-Cl |
| CPM | OH | OH | 4-Me |
| CPM | OH | OH | 5-Me |
| CPM | OH | OH | 6-Me |
| CPM | OH | OH | 7-Me |
| CPM | OH | OH | 5,6-Me |
| CPM | OH | OH | 4-OMe |
| CPM | OH | OH | 5-OMe |
| CPM | OH | OH | 6-OMe |
| CPM | OH | OH | 7-OMe |
| CPM | OH | OH | 5,6-OMe |
| allyl | OH | OH | (non-substituted) |
| allyl | OH | OH | 4-F |
| allyl | OH | OH | 5-F |
| allyl | OH | OH | 6-F |
| allyl | OH | OH | 7-F |
| allyl | OH | OH | 5,6-F |
| allyl | OH | OH | 4,5,6,7-F |
| allyl | OH | OH | 4-Cl |
| allyl | OH | OH | 5-Cl |
| allyl | OH | OH | 6-Cl |
| allyl | OH | OH | 7-Cl |
| allyl | OH | OH | 5,6-Cl |
| allyl | OH | OH | 4-Me |
| allyl | OH | OH | 5-Me |
| allyl | OH | OH | 6-Me |
| allyl | OH | OH | 7-Me |
| allyl | OH | OH | 5,6-Me |
| allyl | OH | OH | 4-OMe |
| allyl | OH | OH | 5-OMe |
| allyl | OH | OH | 6-OMe |
| allyl | OH | OH | 7-OMe |
| allyl | OH | OH | 5,6-OMe |
| CPM | H | OH | (non-substituted) |
| CPM | H | OH | 4-F |
| CPM | H | OH | 5-F |
| CPM | H | OH | 6-F |
| CPM | H | OH | 7-F |
| CPM | H | OH | 5,6-F |
| CPM | H | OH | 4,5,6,7-F |
| CPM | H | OH | 4-Cl |
| CPM | H | OH | 5-Cl |
| CPM | H | OH | 6-Cl |
| CPM | H | OH | 7-Cl |
| CPM | H | OH | 5,6-Cl |
| CPM | H | OH | 4-Me |
| CPM | H | OH | 5-Me |
| CPM | H | OH | 6-Me |
| CPM | H | OH | 7-Me |
| CPM | H | OH | 5,6-Me |
| CPM | H | OH | 4-OMe |
| CPM | H | OH | 5-OMe |
| CPM | H | OH | 6-OMe |
| CPM | H | OH | 7-OMe |
| CPM | H | OH | 5,6-OMe |
| allyl | H | OH | (non-substituted) |
| allyl | H | OH | 4-F |
| allyl | H | OH | 5-F |
| allyl | H | OH | 6-F |
| allyl | H | OH | 7-F |
| allyl | H | OH | 5,6-F |
| allyl | H | OH | 4,5,6,7-F |
| allyl | H | OH | 4-Cl |
| allyl | H | OH | 5-Cl |
| allyl | H | OH | 6-Cl |
| allyl | H | OH | 7-Cl |
| allyl | H | OH | 5,6-Cl |
| allyl | H | OH | 4-Me |
| allyl | H | OH | 5-Me |
| allyl | H | OH | 6-Me |
| allyl | H | OH | 7-Me |

TABLE 3-continued

| R¹ | R² | R³ | R⁵ |
|---|---|---|---|
| allyl | H | OH | 5,6-Me |
| allyl | H | OH | 4-OMe |
| allyl | H | OH | 5-OMe |
| allyl | H | OH | 6-OMe |
| allyl | H | OH | 7-OMe |
| allyl | H | OH | 5,6-OMe |
| CPM | OH | OH | (non-substituted) |
| CPM | OH | OH | 4-F |
| CPM | OH | OH | 5-F |
| CPM | OH | OH | 6-F |
| CPM | OH | OH | 7-F |
| CPM | OH | OH | 5,6-F |
| CPM | OH | OH | 4,5,6,7-F |
| CPM | OH | OH | 4-Cl |
| CPM | OH | OH | 5-Cl |
| CPM | OH | OH | 6-Cl |
| CPM | OH | OH | 7-Cl |
| CPM | OH | OH | 5,6-Cl |
| CPM | OH | OH | 4-Me |
| CPM | OH | OH | 5-Me |
| CPM | OH | OH | 6-Me |
| CPM | OH | OH | 7-Me |
| CPM | OH | OH | 5,6-Me |
| CPM | OH | OH | 4-OMe |
| CPM | OH | OH | 5-OMe |
| CPM | OH | OH | 6-OMe |
| CPM | OH | OH | 7-OMe |
| CPM | OH | OH | 5,6-OMe |
| allyl | OH | OH | (non-substituted) |
| allyl | OH | OH | 4-F |
| allyl | OH | OH | 5-F |
| allyl | OH | OH | 6-F |
| allyl | OH | OH | 7-F |
| allyl | OH | OH | 5,6-F |
| allyl | OH | OH | 4,5,6,7-F |
| allyl | OH | OH | 4-Cl |
| allyl | OH | OH | 5-Cl |
| allyl | OH | OH | 6-Cl |
| allyl | OH | OH | 7-Cl |
| allyl | OH | OH | 5,6-Cl |
| allyl | OH | OH | 4-Me |
| allyl | OH | OH | 5-Me |
| allyl | OH | OH | 6-Me |
| allyl | OH | OH | 7-Me |
| allyl | OH | OH | 5,6-Me |
| allyl | OH | OH | 4-OMe |
| allyl | OH | OH | 5-OMe |
| allyl | OH | OH | 6-OMe |
| allyl | OH | OH | 7-OMe |
| allyl | OH | OH | 5,6-OMe |
| CPM | H | OH | (non-substituted) |
| CPM | H | OH | 4-F |
| CPM | H | OH | 5-F |
| CPM | H | OH | 6-F |
| CPM | H | OH | 7-F |
| CPM | H | OH | 5,6-F |
| CPM | H | OH | 4,5,6,7-F |
| CPM | H | OH | 4-Cl |
| CPM | H | OH | 5-Cl |
| CPM | H | OH | 6-Cl |
| CPM | H | OH | 7-Cl |
| CPM | H | OH | 5,6-Cl |
| CPM | H | OH | 4-Me |
| CPM | H | OH | 5-Me |
| CPM | H | OH | 6-Me |
| CPM | H | OH | 7-Me |
| CPM | H | OH | 5,6-Me |
| CPM | H | OH | 4-OMe |
| CPM | H | OH | 5-OMe |
| CPM | H | OH | 6-OMe |
| CPM | H | OH | 7-OMe |
| CPM | H | OH | 5,6-OMe |
| allyl | H | OH | (non-substituted) |
| allyl | H | OH | 4-F |
| allyl | H | OH | 5-F |
| allyl | H | OH | 6-F |
| allyl | H | OH | 7-F |
| allyl | H | OH | 5,6-F |
| allyl | H | OH | 4,5,6,7-F |
| allyl | H | OH | 4-Cl |
| allyl | H | OH | 5-Cl |
| allyl | H | OH | 6-Cl |
| allyl | H | OH | 7-Cl |
| allyl | H | OH | 5,6-Cl |
| allyl | H | OH | 4-Me |
| allyl | H | OH | 5-Me |
| allyl | H | OH | 6-Me |
| allyl | H | OH | 7-Me |
| allyl | H | OH | 5,6-Me |
| allyl | H | OH | 4-OMe |
| allyl | H | OH | 5-OMe |
| allyl | H | OH | 6-OMe |
| allyl | H | OH | 7-OMe |
| allyl | H | OH | 5,6-OMe |
| CPM | OH | OH | (non-substituted) |
| CPM | OH | OH | 4-F |
| CPM | OH | OH | 5-F |
| CPM | OH | OH | 6-F |
| CPM | OH | OH | 7-F |
| CPM | OH | OH | 5,6-F |
| CPM | OH | OH | 4,5,6,7-F |
| CPM | OH | OH | 4-Cl |
| CPM | OH | OH | 5-Cl |
| CPM | OH | OH | 6-Cl |
| CPM | OH | OH | 7-Cl |
| CPM | OH | OH | 5,6-Cl |
| CPM | OH | OH | 4-Me |
| CPM | OH | OH | 5-Me |
| CPM | OH | OH | 6-Me |
| CPM | OH | OH | 7-Me |
| CPM | OH | OH | 5,6-Me |
| CPM | OH | OH | 4-OMe |
| CPM | OH | OH | 5-OMe |
| CPM | OH | OH | 6-OMe |
| CPM | OH | OH | 7-OMe |
| CPM | OH | OH | 5,6-OMe |
| allyl | OH | OH | (non-substituted) |
| allyl | OH | OH | 4-F |
| allyl | OH | OH | 5-F |
| allyl | OH | OH | 6-F |
| allyl | OH | OH | 7-F |
| allyl | OH | OH | 5,6-F |
| allyl | OH | OH | 4,5,6,7-F |
| allyl | OH | OH | 4-Cl |
| allyl | OH | OH | 5-Cl |
| allyl | OH | OH | 6-Cl |
| allyl | OH | OH | 7-Cl |
| allyl | OH | OH | 5,6-Cl |
| allyl | OH | OH | 4-Me |
| allyl | OH | OH | 5-Me |
| allyl | OH | OH | 6-Me |
| allyl | OH | OH | 7-Me |
| allyl | OH | OH | 5,6-Me |
| allyl | OH | OH | 4-OMe |
| allyl | OH | OH | 5-OMe |
| allyl | OH | OH | 6-OMe |
| allyl | OH | OH | 7-OMe |
| allyl | OH | OH | 5,6-OMe |
| CPM | H | OH | (non-substituted) |
| CPM | H | OH | 4-F |
| CPM | H | OH | 5-F |
| CPM | H | OH | 6-F |
| CPM | H | OH | 7-F |
| CPM | H | OH | 5,6-F |
| CPM | H | OH | 4,5,6,7-F |
| CPM | H | OH | 4-Cl |
| CPM | H | OH | 5-Cl |
| CPM | H | OH | 6-Cl |
| CPM | H | OH | 7-Cl |
| CPM | H | OH | 5,6-Cl |
| CPM | H | OH | 4-Me |
| CPM | H | OH | 5-Me |
| CPM | H | OH | 6-Me |
| CPM | H | OH | 7-Me |

TABLE 3-continued

| R¹ | R² | R³ | R⁵ |
|---|---|---|---|
| CPM | H | OH | 5,6-Me |
| CPM | H | OH | 4-OMe |
| CPM | H | OH | 5-OMe |
| CPM | H | OH | 6-OMe |
| CPM | H | OH | 7-OMe |
| CPM | H | OH | 5,6-OMe |
| allyl | H | OH | (non-substituted) |
| allyl | H | OH | 4-F |
| allyl | H | OH | 5-F |
| allyl | H | OH | 6-F |
| allyl | H | OH | 7-F |
| allyl | H | OH | 5,6-F |
| allyl | H | OH | 4,5,6,7-F |
| allyl | H | OH | 4-Cl |
| allyl | H | OH | 5-Cl |
| allyl | H | OH | 6-Cl |
| allyl | H | OH | 7-Cl |
| allyl | H | OH | 5,6-Cl |
| allyl | H | OH | 4-Me |
| allyl | H | OH | 5-Me |
| allyl | H | OH | 6-Me |
| allyl | H | OH | 7-Me |
| allyl | H | OH | 5,6-Me |
| allyl | H | OH | 4-OMe |
| allyl | H | OH | 5-OMe |
| allyl | H | OH | 6-OMe |
| allyl | H | OH | 7-OMe |
| allyl | H | OH | 5,6-OMe |

Among the compounds represented by Formula (I), specific examples of the compounds wherein —X— is a carbon chain having two carbon atoms constituting a part of the ring structure, Y and Z are —C(=O), two R⁴s form cyclohexene fused ring which is not substituted or substituted by one or more R⁵s, R⁹ hydrogen, R¹⁰ and R¹¹ are bound to form —O—, that is, the examples of the compounds represented by the following Formula (Id) are shown in Table 4.

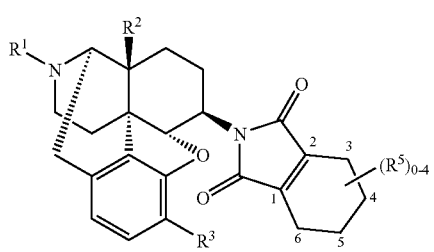
(Id)

Among the compounds represented by Formula (Id), the compound wherein R¹ is cyclopropylmethyl, R² and R³ are hydroxy, the cyclohexene ring is not substituted, and the configuration of the bond at the 6-position is β, that is, the compound of the following formula:

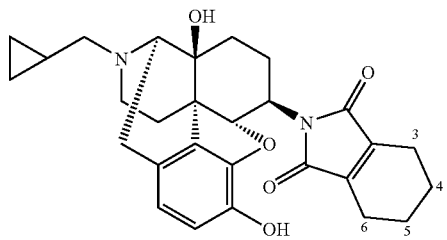

is named N-[17-(cyclopropylmethyl)-4,5α-epoxy-3,14-dihydroxymorphinan-6β-yl]-3,4,5,6-tetrahydrophthalimide.

TABLE 4

| R¹ | R² | R³ | R⁵ |
|---|---|---|---|
| CPM | OH | OH | (non-substituted) |
| CPM | OH | OH | 3-F |
| CPM | OH | OH | 4-F |
| CPM | OH | OH | 3,6-F |
| CPM | OH | OH | 4,5-F |
| CPM | OH | OH | 3,4,5,6-F |
| CPM | OH | OH | 3-Cl |
| CPM | OH | OH | 4-Cl |
| CPM | OH | OH | 3,6-Cl |
| CPM | OH | OH | 4,5-Cl |
| CPM | OH | OH | 3-Br |
| CPM | OH | OH | 4-Br |
| CPM | OH | OH | 3,6-Br |
| CPM | OH | OH | 4,5-Br |
| CPM | OH | OH | 3-Me |
| CPM | OH | OH | 4-Me |
| CPM | OH | OH | 3,6-Me |
| CPM | OH | OH | 4,5-Me |
| CPM | OH | OH | 3-OMe |
| CPM | OH | OH | 4-OMe |
| CPM | OH | OH | 3,6-OMe |
| CPM | OH | OH | 4,5-OMe |
| CPM | OH | OH | 3-OH |
| CPM | OH | OH | 4-OH |
| CPM | OH | OH | 3,6-OH |
| CPM | OH | OH | 4,5-OH |
| CPM | OH | OH | 3-NO₂ |
| CPM | OH | OH | 4-NO₂ |
| CPM | OH | OH | 3,6-NO₂ |
| CPM | OH | OH | 4,5-NO₂ |
| CPM | OH | OH | 3-NH₂ |
| CPM | OH | OH | 4-NH₂ |
| CPM | OH | OH | 3,6-NH₂ |
| CPM | OH | OH | 4,5-NH₂ |
| allyl | OH | OH | (non-substituted) |
| allyl | OH | OH | 3-F |
| allyl | OH | OH | 4-F |
| allyl | OH | OH | 3,6-F |
| allyl | OH | OH | 4,5-F |
| allyl | OH | OH | 3,4,5,6-F |
| allyl | OH | OH | 3-Cl |
| allyl | OH | OH | 4-Cl |
| allyl | OH | OH | 3,6-Cl |
| allyl | OH | OH | 4,5-Cl |
| allyl | OH | OH | 3-Br |
| allyl | OH | OH | 4-Br |
| allyl | OH | OH | 3,6-Br |
| allyl | OH | OH | 4,5-Br |
| allyl | OH | OH | 3-Me |
| allyl | OH | OH | 4-Me |
| allyl | OH | OH | 3,6-Me |
| allyl | OH | OH | 4,5-Me |
| allyl | OH | OH | 3-OMe |
| allyl | OH | OH | 4-OMe |
| allyl | OH | OH | 3,6-OMe |
| allyl | OH | OH | 4,5-OMe |
| allyl | OH | OH | 3-OH |
| allyl | OH | OH | 4-OH |

TABLE 4-continued

| R¹ | R² | R³ | R⁵ |
|---|---|---|---|
| allyl | OH | OH | 3,6-OH |
| allyl | OH | OH | 4,5-OH |
| allyl | OH | OH | 3-NO₂ |
| allyl | OH | OH | 4-NO₂ |
| allyl | OH | OH | 3,6-NO₂ |
| allyl | OH | OH | 4,5-NO₂ |
| allyl | OH | OH | 3-NH₂ |
| allyl | OH | OH | 4-NH₂ |
| allyl | OH | OH | 3,6-NH₂ |
| allyl | OH | OH | 4,5-NH₂ |
| CPM | H | OH | (non-substituted) |
| CPM | H | OH | 3-F |
| CPM | H | OH | 4-F |
| CPM | H | OH | 3,6-F |
| CPM | H | OH | 4,5-F |
| CPM | H | OH | 3,4,5,6-F |
| CPM | H | OH | 3-Cl |
| CPM | H | OH | 4-Cl |
| CPM | H | OH | 3,6-Cl |
| CPM | H | OH | 4,5-Cl |
| CPM | H | OH | 3-Br |
| CPM | H | OH | 4-Br |
| CPM | H | OH | 3,6-Br |
| CPM | H | OH | 4,5-Br |
| CPM | H | OH | 3-Me |
| CPM | H | OH | 4-Me |
| CPM | H | OH | 3,6-Me |
| CPM | H | OH | 4,5-Me |
| CPM | H | OH | 3-OMe |
| CPM | H | OH | 4-OMe |
| CPM | H | OH | 3,6-OMe |
| CPM | H | OH | 4,5-OMe |
| CPM | H | OH | 3-OH |
| CPM | H | OH | 4-OH |
| CPM | H | OH | 3,6-OH |
| CPM | H | OH | 4,5-OH |
| CPM | H | OH | 3-NO₂ |
| CPM | H | OH | 4-NO₂ |
| CPM | H | OH | 3,6-NO₂ |
| CPM | H | OH | 4,5-NO₂ |
| CPM | H | OH | 3-NH₂ |
| CPM | H | OH | 4-NH₂ |
| CPM | H | OH | 3,6-NH₂ |
| CPM | H | OH | 4,5-NH₂ |
| allyl | H | OH | (non-substituted) |
| allyl | H | OH | 3-F |
| allyl | H | OH | 4-F |
| allyl | H | OH | 3,6-F |
| allyl | H | OH | 4,5-F |
| allyl | H | OH | 3,4,5,6-F |
| allyl | H | OH | 3-Cl |
| allyl | H | OH | 4-Cl |
| allyl | H | OH | 3,6-Cl |
| allyl | H | OH | 4,5-Cl |
| allyl | H | OH | 3-Br |
| allyl | H | OH | 4-Br |
| allyl | H | OH | 3,6-Br |
| allyl | H | OH | 4,5-Br |
| allyl | H | OH | 3-Me |
| allyl | H | OH | 4-Me |
| allyl | H | OH | 3,6-Me |
| allyl | H | OH | 4,5-Me |
| allyl | H | OH | 3-OMe |
| allyl | H | OH | 4-OMe |
| allyl | H | OH | 3,6-OMe |
| allyl | H | OH | 4,5-OMe |
| allyl | H | OH | 3-OH |
| allyl | H | OH | 4-OH |
| allyl | H | OH | 3,6-OH |
| allyl | H | OH | 4,5-OH |
| allyl | H | OH | 3-NO₂ |
| allyl | H | OH | 4-NO₂ |
| allyl | H | OH | 3,6-NO₂ |
| allyl | H | OH | 4,5-NO₂ |
| allyl | H | OH | 3-NH₂ |
| allyl | H | OH | 4-NH₂ |
| allyl | H | OH | 3,6-NH₂ |
| allyl | H | OH | 4,5-NH₂ |
| CPM | OAc | OH | (non-substituted) |
| CPM | OAc | OH | 3-F |
| CPM | OAc | OH | 4-F |
| CPM | OAc | OH | 3,6-F |
| CPM | OAc | OH | 4,5-F |
| CPM | OAc | OH | 3,4,5,6-F |
| CPM | OAc | OH | 3-Cl |
| CPM | OAc | OH | 4-Cl |
| CPM | OAc | OH | 3,6-Cl |
| CPM | OAc | OH | 4,5-Cl |
| CPM | OAc | OH | 3-Br |
| CPM | OAc | OH | 4-Br |
| CPM | OAc | OH | 3,6-Br |
| CPM | OAc | OH | 4,5-Br |
| CPM | OAc | OH | 3-Me |
| CPM | OAc | OH | 4-Me |
| CPM | OAc | OH | 3,6-Me |
| CPM | OAc | OH | 4,5-Me |
| CPM | OAc | OH | 3-OMe |
| CPM | OAc | OH | 4-OMe |
| CPM | OAc | OH | 3,6-OMe |
| CPM | OAc | OH | 4,5-OMe |
| CPM | OAc | OH | 3-OH |
| CPM | OAc | OH | 4-OH |
| CPM | OAc | OH | 3,6-OH |
| CPM | OAc | OH | 4,5-OH |
| CPM | OAc | OH | 3-NO₂ |
| CPM | OAc | OH | 4-NO₂ |
| CPM | OAc | OH | 3,6-NO₂ |
| CPM | OAc | OH | 4,5-NO₂ |
| CPM | OAc | OH | 3-NH₂ |
| CPM | OAc | OH | 4-NH₂ |
| CPM | OAc | OH | 3,6-NH₂ |
| CPM | OAc | OH | 4,5-NH₂ |
| allyl | OAc | OH | (non-substituted) |
| allyl | OAc | OH | 3-F |
| allyl | OAc | OH | 4-F |
| allyl | OAc | OH | 3,6-F |
| allyl | OAc | OH | 4,5-F |
| allyl | OAc | OH | 3,4,5,6-F |
| allyl | OAc | OH | 3-Cl |
| allyl | OAc | OH | 4-Cl |
| allyl | OAc | OH | 3,6-Cl |
| allyl | OAc | OH | 4,5-Cl |
| allyl | OAc | OH | 3-Br |
| allyl | OAc | OH | 4-Br |
| allyl | OAc | OH | 3,6-Br |
| allyl | OAc | OH | 4,5-Br |
| allyl | OAc | OH | 3-Me |
| allyl | OAc | OH | 4-Me |
| allyl | OAc | OH | 3,6-Me |
| allyl | OAc | OH | 4,5-Me |
| allyl | OAc | OH | 3-OMe |
| allyl | OAc | OH | 4-OMe |
| allyl | OAc | OH | 3,6-OMe |
| allyl | OAc | OH | 4,5-OMe |
| allyl | OAc | OH | 3-OH |
| allyl | OAc | OH | 4-OH |
| allyl | OAc | OH | 3,6-OH |
| allyl | OAc | OH | 4,5-OH |
| allyl | OAc | OH | 3-NO₂ |
| allyl | OAc | OH | 4-NO₂ |
| allyl | OAc | OH | 3,6-NO₂ |
| allyl | OAc | OH | 4,5-NO₂ |
| allyl | OAc | OH | 3-NH₂ |
| allyl | OAc | OH | 4-NH₂ |
| allyl | OAc | OH | 3,6-NH₂ |
| allyl | OAc | OH | 4,5-NH₂ |

The morphinan derivatives represented by the above-described Formula (I), having a nitrogen-containing cyclic group used as the effective ingredient of the antipruritic according to the present invention may be produced by the methods hereinbelow described.

Among the compounds represented by the Formula (I), the cyclic imide and sulfoneimide derivatives represented by Formula (IA) (wherein $R^1$, $R^2$, $R^3$, $R^5$, $R^9$, $R^{10}$ and $R^{11}$ represent the same meanings as described above, and the broken lines represent single bond or aromatic fused ring) may be produced by reacting a primary amine represented by Formula (II) (wherein $R^1$, $R^2$, $R^3$, $R^9$, $R^{10}$ and $R^{11}$ represent the same meanings as described above) and an acid anhydride represented by Formula (III) (wherein $R^5$ represents the same meanings as described above) or a sulfonic acid derivative represented by Formula (III') (wherein $R^{20}$ represents $C_1$-$C_5$ alkyl, and $R^5$ represents the same meaning as described above), as shown in Scheme 1. As required, the reaction may be carried out in the presence of an acid or a base.

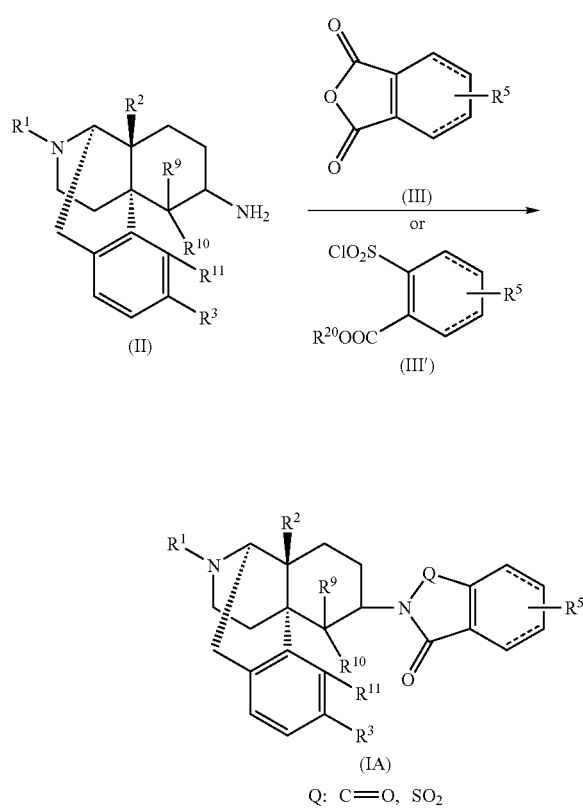

Q: C=O, SO$_2$

The acid anhydride (III) or the sulfonic acid derivative (III') may be used in an amount of 0.5 to 50 equivalents, preferably 1 to 20 equivalents, with respect to the primary amine (II. When $R^3$ is hydroxy, the hydroxy group may be protected by an appropriate protective group such as methoxymethyl), and especially, good results are obtained when they are used in an amount of 1 to 10 equivalents. As the solvent, aprotic polar solvents such as DMF, dimethylacetamide and DMSO; ether solvents such as diethylether, THF, DME and dioxane; hydrocarbon solvents such as benzene, toluene and xylene; halogen-containing solvents such as dichloromethane, chloroform and 1,2-dichloroethane; alcohols such as methanol, ethanol, propanol and butanol; and acid solvents such as acetic acid and propionic acid may be employed. Among these, DMF, toluene, acetic acid and chloroform are preferred.

As the base to be made to coexist as required, inorganic bases such as sodium carbonate, potassium carbonate, cesium carbonate and sodium acetate; and organic bases such as triethylamine, diisopropylethylamine, pyridine and 4-dimethylaminopyridine may be used. Among these, triethylamine, pyridine, potassium carbonate and sodium carbonate are preferred. The base is used in amount of 1 to 30 equivalents, preferably 1 to 10 equivalents with respect to the substrate. On the other hand, as the acid, inorganic acids such as hydrochloric acid, sulfuric acid and phosphoric acid; carboxylic acids such as acetic acid, propionic acid and benzoic acid; and sulfonic acids such as methanesulfonic acid, benzenesulfonic acids and p-toluenesulfonic acid may be used. Among these, carboxylic acids such as acetic acid, propionic acid and benzoic acid are preferred, and acetic acid is especially preferred. The acid is used in amount of 1 to 30 equivalents, preferably 1 to 10 equivalents with respect to the substrate. A process in which acetic acid or the like is used as the solvent is also preferred. In this case, excessive acid coexists.

The reaction may usually be carried out at −20° C. to 200° C. and preferably at 0° C. to 150° C. at which satisfactory results are obtained. The reaction time may appropriately be selected depending on the conditions such as reaction temperature, satisfactory results are usually obtained when the reaction time is about 30 minutes to 30 hours. The concentration of the substrate (II) in the reaction system is not restricted, and usually about 1 mmol/L to 1 mol/L is preferred.

The primary amine represented by Formula (II) used as the starting material of Scheme 1 may be synthesized by the method described in, for example, J. Med. Chem. 20, 1100 (1977). J. Org. Chem. 45, 3366 (1980).

Among the compounds represented by Formula (IA) (wherein $R^1$, $R^2$, $R^3$, $R^5$, $R^9$, $R^{10}$ and $R^{11}$ represent the same meanings as described above), the imide derivatives may also be produced by Mitsunobu reaction described in Tetrahedron. 50, 9757 (1994).

Among the compounds represented by Formula (I), the cyclic amide compounds (IB) (wherein $R^1$, $R^2$, $R^3$, $R^4$, $R^9$, $R^{10}$, $R^{11}$, k and X represent the same meanings as described above) wherein Y is —C(=O)— and Z is valence bond may be produced by the usual alkylation reaction of amide group or amidation reaction of amino group so as to attain intramolecular cyclization, from the compound represented by Formula (IV) (wherein $R^1$, $R^2$, $R^3$, $R^4$, $R^9$, $R^{10}$, $R^{11}$, k and X represent the same meanings as described above, L is chlorine, bromine, iodine, OTs or OMs) or the compound represented by Formula (V) (wherein $R^1$, $R^2$, $R^3$, $R^4$, $R^9$, $R^{10}$, $R^{11}$, k and X represent the same meanings as described above, L' is chlorine or $OR^{12}$ (wherein $R^{12}$ is hydrogen, $C_1$-$C_5$ alkoxy, $C_7$-$C_{13}$ aralkyloxy or $C_1$-$C_5$ alkanoyloxy), as shown by Scheme 2 below. The compounds represented by Formula (IV) or (V) used as the starting materials of the reaction shown in Scheme 2 may be obtained by the method described in WO93/15081 and so on.

Scheme 2

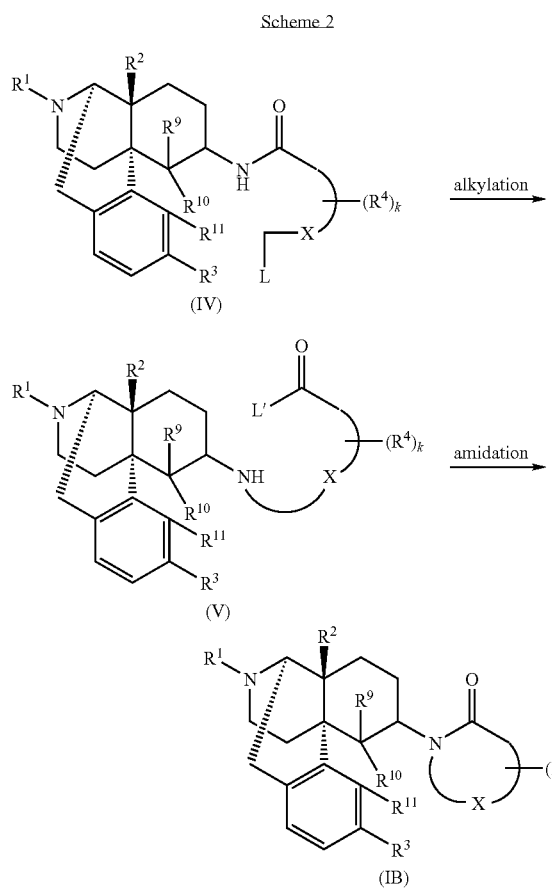

Scheme 3

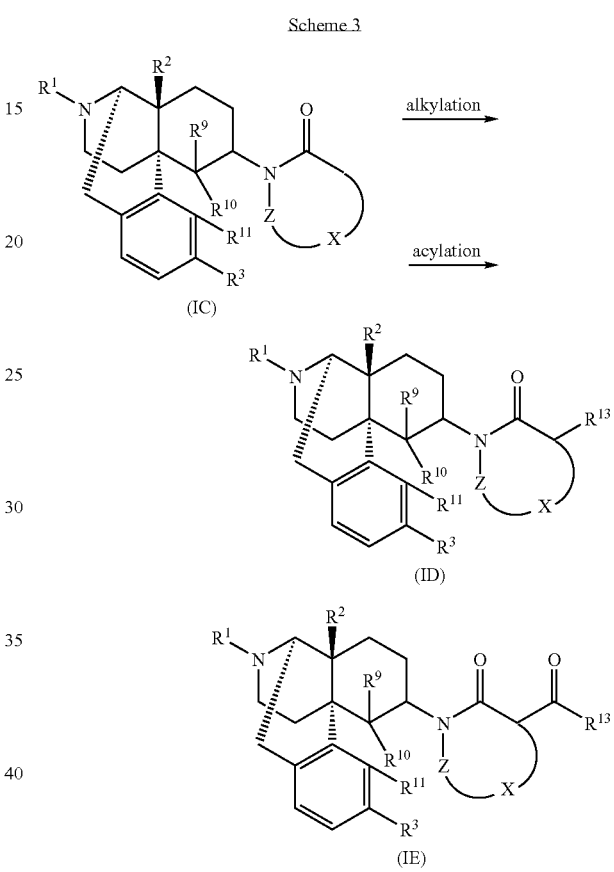

by Formula (ID) or (IE) (wherein $R^1$, $R^2$, $R^3$, $R^9$, $R^{10}$, $R^{11}$, X and Z represent the same meanings as described above, $R^{13}$ is $C_1$-$C_5$ alkyl or $C_7$-$C_{13}$ aralkyl) may be produced by alkylating or acylating the compounds represented by Formula (IC) (wherein $R^1$, $R^2$, $R^3$, $R^9$, $R^{10}$, $R^{11}$, X and Z represent the same meanings as described above) in a solvent in the co-presence of a base, as shown in Scheme 3 below. The compounds of Formula (IC) used as a starting material of Scheme 3 may be obtained by the methods shown in Schemes 1 and 2.

The alkylation or amidation may be carried out by a general method in which a base is made to coexist in a solvent.

As the base, inorganic bases such as potassium carbonate, cesium carbonate, sodium hydroxide and potassium hydroxide; metal hydrides such as sodium hydride and potassium hydride; metal alkoxides such as sodium ethoxide and potassium t-butoxide; and organic bases such as triethylamine, diisopropylethylamine, pyridine and 4-dimethylaminopyridine may be used. The base is used in an amount of 1 to 30 equivalents, preferably 1 to 10 equivalents with respect to the substrate. In case of amidation reaction, satisfactory results may be obtained without using a base in some cases.

As the solvent, aprotic polar solvents such as DMF, dimethylacetoamide and DMSO; ether solvents such as diethyl ether, THF, DME and dioxane; hydrocarbon solvents such as benzene and toluene; and halogen-containing solvents such as dichloromethane, chloroform and 1,2-dichloroethane may be used. Among these, DMF, THF and toluene are preferred. As for the reaction temperature, satisfactory results may be usually obtained at −20° C. to 200° C., preferably 0° C. to 150° C. The reaction time is appropriately selected depending on the conditions such as reaction temperature, and satisfactory results are usually obtained when the reaction time is about 30 minutes to 100 hours. The concentration of the substrate (IV) or (V) in the reaction mixture is not restricted, and usually 1 mmol/L to 1 mol/L is preferred.

Among the compounds represented by Formula (I) (wherein $R^1$, $R^2$, $R^3$, $R^4$, $R^9$, $R^{10}$, $R^{11}$, X, Y, Z and k represent the same meanings as described above), the compounds wherein Y is —C(=O)—, that is, the compounds represented An alkylation agent or acylation agent may preferably be used in an amount of 1 to 20 equivalents, and satisfactory results are obtained by using the alkylation agent or acylation agent in an amount of 1 to 10 equivalents.

As the base, organic lithium reagents such as methyl lithium, butyl lithium and LDA; metal hydrides such as sodium hydride and potassium hydride; and metal alkoxide such as sodium ethoxide, potassium t-butoxide may be used, and LDA and butyl lithium are preferred. The base may be used in an amount of 1 to 30 equivalents, preferably 1 to 10 equivalents with respect to the substrate.

As the solvent, aprotic polar solvents such as DMF, dimethylacetoamide and DMSO; ether solvents such as diethyl ether, THF, DME and dioxane; and hydrocarbon solvents such as pentane, hexane, benzene and toluene may be used. Among these, THF and DME are preferred.

As for the reaction temperature, satisfactory results may be usually obtained at −100° C. to 200° C., preferably −80° C. to 150° C. The reaction time is appropriately selected depending on the conditions such as reaction temperature, and satisfactory results are usually obtained when the reaction time is about 30 minutes to 30 hours. The concentration of the substrate (IC) in the reaction mixture is not restricted, and usually 1 mmol/L to 1 mol/L is preferred.

When synthesizing the compounds represented by Formula (I) wherein $R^3$ is hydroxy, that is, the compounds represented by Formula (IG) (wherein $R^1$, $R^2$, $R^4$, $R^9$, $R^{10}$, $R^{11}$, X, Y, Z and k represent the same meanings as described above), the compounds may be synthesized through the compounds of Formula (IF) (wherein $R^1$, $R^2$, $R^4$, $R^9$, $R^{10}$, $R^{11}$, X, Y, Z and k represent the same meanings as described above), wherein $R^3$ is methoxy, in order to protect the phenol moiety. In this case, the deprotection may be carried out by the usual demethylation reaction of phenolic methyl ether, as shown in Scheme 4, more particularly, by (1) a method in which boron tribromide is used, or (2) a method in which an alkylthiol is used under basic condition.

Scheme 4

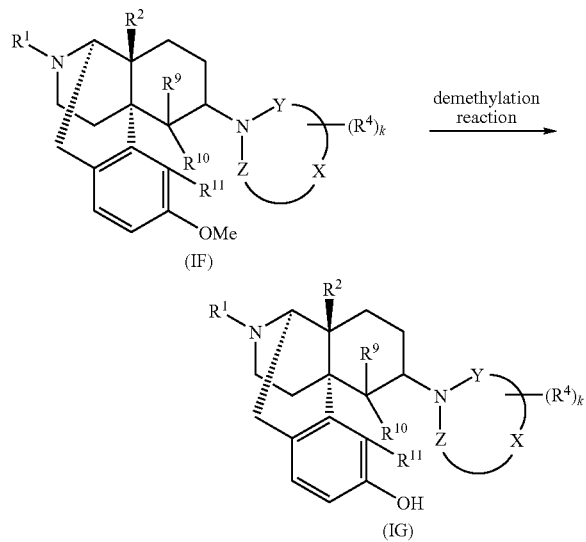

In the method (1), the amount of the boron tribromide is preferably 1 to 20 equivalents, and satisfactory results are obtained by using boron tribromide in an amount of 1 to 7 equivalents. As the reaction solvent, halogen-containing solvents such as dichloromethane, chloroform and 1,2-dichloroethane are preferred, and dichloromethane is preferred. The reaction temperature is preferably −70° C. to 50° C., and satisfactory results are obtained when the reaction temperature is −50° C. to 40° C. The reaction time is preferably 10 minutes to 10 hours, and satisfactory results are obtained when the reaction time is 30 minutes to 5 hours. The concentration of the compound (IF) in the reaction system is not restricted, and usually 1 mmol/L to 1 mol/L is preferred.

In the method (2), as the reagent, an alkylthiol such as ethanethiol, propanethiol or butanethiol is preferred, and propanethiol is especially preferred. The amount of the alkylthiol is preferably 1 to 20 equivalents, and satisfactory results are obtained by using alkylthiol in an amount of 1 to 7 equivalents. As the base, potassium t-butoxide, sodium hydride and potassium hydride are preferred, and potassium t-butoxide is especially preferred. The amount of the base is preferably 1 to 20 equivalents, and satisfactory results are obtained by using the base in an amount of 1 to 7 equivalents. As the reaction solvent, aprotic polar solvents such as DMF and dimethylacetoamide; and ether solvents such as THF and DME are preferred, and DMF which is an aprotic solvent is particularly preferred. The reaction temperature is preferably 50° C. to 200° C., and satisfactory results are obtained when the reaction temperature is 80° C. to 150° C. The reaction time is preferably 1 hour to 15 hours, and satisfactory results are obtained when the reaction time is 2 to 8 hours. The concentration of the compound (IF) in the reaction system is not restricted, and usually 1 mmol/L to 1 mol/L is preferred.

The fact that the morphinan derivatives having the nitrogen-containing cyclic group, represented by Formula (I) are effective against pruritus can be confirmed by the fact that they have action to inhibit scratching behavior in animals. Although the action to inhibit scratching behavior in animals may be confirmed by the method described in a reference [Eur. J. Pharmacol., vol 477, 29-35 (2003)], the method is not restricted thereto.

The antipruritic may be used against atopic dermatitis, neurogenic dermatitis, contact dermatitis, seborrheic dermatitis, autosensitization dermatitis, caterpillar dermatitis, asteatosis, senile pruritus, insect sting, photosensitive dermatosis, urticaria, prurigo, herpes blister, impetigo, eczema, tinea, lichen, psoriasis, scabies, and acne vulgaris, as well as against organ diseases and medical treatments accompanying pruritus, such as malignant tumors, diabetes mellitus, hepatic diseases, renal failure, hemodialysis, gout, thyroid diseases, hemopathy and sideropenia. In addition, they may be used against the pruritus due to pregnancy or vermination, and against the pruritus induced by drugs and by psychogenic reasons. The antipruritic may also be applied to the pruritus accompanying ophthalmic or otorhinolaryngologic diseases. The antipruritic may also be applied to mammals (e.g., mouse, rat, hamster, rabbit, cat, dog, bovine, sheep, monkey and human).

When administering the antipruritic, the compound described in the present invention may be administered individually or in combination with one or more substances which are used for the therapy or prevention of the disease, or used for the alleviation or inhibition of the symptoms. Examples of such substances include anthelmintics such as fipronil, lufenuron, imidacloprid, avermectins (e.g., abamectin, ivermectin, doramectin, milbemycins, organic phosphate and pyrethroid; antihistamines such as chlorophenylamine, trimeprazine, diphenhydramine and doxylamine; antifungals such as fluconazole, ketoconazole, itraconazole, griseofulvin and amphotericin B; antibacterial agents such as enrofloxacin, marbofloxacin, ampicillin and amoxicillin; antiinflammatory agents such as prednisolone, betamethasone, carprofen, clobetasol, diflorasone, hydrocortisone, dexamethasone, ketoprofen and meloxicam; antiallergic drugs such as mequitazine, ketotifen, azelastine, oxatomide and fexofenadine; therapeutic agents against atopic dermatitis such as tacrolimus; supplementary foods such as γ-linoleic acid; emollients; and humectant, although the substances are not restricted thereto.

When the antipruritic is clinically used, the drug may be in the form of the free base or its salt per se, or additives such as vehicles, stabilizers, preservatives, buffering agents, solubilizers, emulsifiers, diluents and isotonic agents may be admixed appropriately. Administration forms thereof include oral preparations such as tablets, capsules, granules, powders and syrups; parenteral preparations such as injection solutions, suppositories and liquids; and topical preparations such as ointments, creams and patches. When used for the treatments of dermatoses, external preparations are preferred. The external preparations may be prepared by mixing the effective ingredient with one or more of fats (preferably, plant oils, animal oils, waxes, fatty acids, fatty alcohols, mineral oils, turpentine oils, vaselines, etc.), solvents (preferably, water, ethanol, glycerin, propylene glycol, isopropyl alcohol, ether, etc.), preserving agents (preferably, paraoxybenzoic acid ester, benzoic acid, salicylic acid, sorbic acid, benzalkonium, benzethonium, propyleneglycol, chlorobuthanol, benzyl alcohol, ethanol, etc.), stabilizers (preferably, tocopherol, butylhydroxyanisol, dibutylhydroxytoluene, sulfites, edetic acid disodium, etc.), anionic surfactants (preferably, potassium soap, medical soap, zinc undecylenate, calcium stearate, magnesium stearate, aluminum monostearate, calcium linolate, sodium laurylsulfate, etc.), non-ionic surfactants (preferably, glyceryl monostearate, sorbitan fatty acid partial esters, sugar fatty acid esters, stearic acid polyoxyl 40, macrogolic acids, lauromacrogol, polyoxyethylene 160, polyoxypropylene 30 glycol, polyoxyethylene hardened castor oils, polyoxyethylene sorbitan fatty acid partial esters, etc.), cationic surfactants (preferably, benzalkonium chloride, benzethonium chloride, cetyl piridinium chloride, etc.), powders (preferably, zinc oxide, zinc powder in starch, kaolin, bismuth hyponitrite, titanium oxide, titanium dioxide, sulfur, anhydrous silicic acid, tarc, etc.), preservatives (preferably, paraoxybenzoic acid esters, sorbic acid, p-chloro-m-xylenol, Irgasan, hexachlorophene, etc.), emulsifiers (preferably, arabic gum powder, tragacanth powder, bentonite, carboxymethylcellulose sodium, methylcellulose, etc.), and moisturizers (preferably, glycerin, propylene glycol, polyethylene glycol, 1,3-butylene glycol, sorbitol, polypyrrolidone carboxylic acid sodium, sodium lactate, sodium hyaluronate, chitin derivatives, urea, amino acids, sugar amino acids, etc) to form a base, and formulating the base into the form of ointment, cream, pack, liniment or patch. The preparation may also be in the form of external liquid. Further, the preparation may be made as a solution for topical ophthalmic use.

The antipruritic preferably contains the effective ingredient in an amount of 0.00001 to 90% by weight, more preferably 0.0001 to 70% by weight. Although the administration dose is appropriately selected depending on the symptom, age, body weight, administration method and the like, in case of injection solution or external preparation, 0.1 μg to 1 g per day for an adult, and in case of oral preparation, 1 μg to 10 g per day for an adult, in terms of the amount of the effective ingredient, may be administered at one time or in several times.

Our compounds and methods will now be described concretely by way of examples.

EXAMPLES

Reference Example 1

Synthesis of N-[(17-cyclopropylmethyl)-4,5α-epoxy-3,14-dihydroxy-morphinan-6β-yl]-phthalimide hydrochloric acid salt (Compound 1)

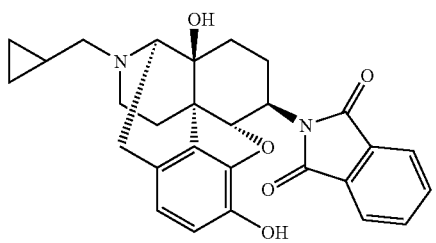

In 7 mL of DMF, 150 mg (0.44 mmol) of 6β-naltrexamine was dissolved, and 71 mg (0.48 mmol) of phthalic anhydride and 0.92 mL (0.66 mmol) of triethylamine were added, followed by stirring the mixture at 140° C. for 4 hours. After allowing the reaction solution to cool to room temperature, saturated aqueous sodium hydrogen carbonate solution was added and the resulting mixture was extracted with ethyl acetate. Organic layers were combined, washed with water and saturated saline, dried over anhydrous magnesium sulfate, and concentrated to obtain a crude product. The obtained crude product was purified by silica gel column chromatography to obtain 120 mg (yield: 58%) of free base compound (6). An aliquot thereof was converted to hydrochloric acid salt to obtain the captioned compound 1.

$^1$H-NMR (ppm) (300 MHz, CDCl$_3$)

7.8-7.9 (2H, m), 7.7-7.8 (2H, m), 6.76 (1H, d, J=7.9 Hz), 6.63 (1H, d, J=8.2 Hz), 5.18 (1H, d, J=8.5 Hz), 4.0-4.1 (1H, m), 3.11 (1H, d, J=5.6 Hz), 3.05 (1H, d, J=18.8 Hz), 2.6-2.9 (3H, m), 2.3-2.4 (3H, m), 2.15 (1H, dt, J=12.0, 3.5 Hz), 1.4-1.7 (4H, m), 0.8-0.9 (1H, m), 0.5-0.6 (2H, m), 0.1-0.2 (2H, m) (free form)

IR (cm$^{-1}$) (KBr)

3320, 1769, 1708, 1626, 1504, 1466, 1428, 1379, 1323, 1271, 1240, 1190, 1173, 1075

Elementary Analysis:

Formula: C28H28N2O5.1.0HCl.1.0H2O

Calcd.: C, 63.81; H, 5.93; N, 5.32, Cl, 6.73.

Found: C, 63.72; H, 6.03; N, 5.40, Cl, 6.49.

Mass (EI): 472 (M$^+$)

Reference Example 2

Synthesis of N-[(17-allyl)-4,5α-epoxy-3,14-dihydroxy-morphinan-6β-yl]-phthalimide tartaric acid salt (Compound 2)

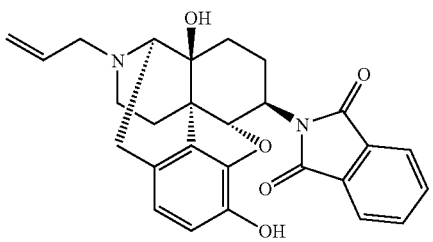

The same procedure as in Reference Example 1 was repeated except that 6β-naloxamine was used in place of 6β-naltrexamine to obtain 24 mg (yield: 34%) of free form of Compound 2. This product was converted to tartaric acid salt to obtain the captioned compound 2.

$^1$H-NMR (ppm) (300 MHz, CDCl$_3$)

7.75-7.8 (2H, m), 7.6-7.7 (2H, m), 6.72 (1H, d, J=8.2 Hz), 6.59 (1H, d, J=8.2 Hz), 5.7-5.8 (1H, m), 5.1-5.2 (3H, m), 4.0-4.05 (1H, m), 3.0-3.1 (3H, m), 2.45-2.9 (5H, m), 2.0-2.3 (2H, m), 1.6-1.7 (1H, m), 1.4-1.5 (2H, m) (free form)

Mass (ESI): 459 (M$^+$+1)

Reference Example 3

Synthesis of N-[(17-cyclopropylmethyl)-4,5α-epoxy-3,14-dihydroxy-morphinan-6β-yl]-3,4,5,6-tetrahydrophthalimide tartaric acid salt (Compound 3)

3

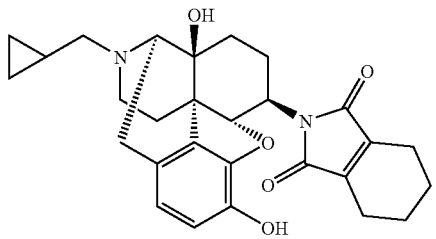

In 3.3 mL of chloroform, 113 mg (0.33 mmol) of 6β-naltrexamine was dissolved, and 58 mg (0.38 mmol) of 3,4,5,6-tetrahydrophthalic anhydride and 114 μL (0.82 mmol) of triethylamine were added, followed by stirring the mixture at room temperature for 50 minutes. Thereafter, 234 μL (1.68 mmol) of triethylamine and 158 μL (1.68 mmol) of acetic anhydride were added to this reaction solution, followed by heating the solution to reflux for 1 hour. After allowing the reaction solution to cool to room temperature, the solution was concentrated by an evaporator, and then 3 mL of methanol and 300 μL of 28% aqueous ammonia were added, followed by stirring the mixture at room temperature for 4 hours. Thereafter, water was added and the resulting mixture was extracted with chloroform. Organic layers were combined, washed with water and saturated saline, dried over anhydrous magnesium sulfate and concentrated to obtain a crude product. The obtained crude product was purified by silica gel column chromatography to obtain 121 mg (yield: 77%) of free form of compound 3. This product was converted to methanesulfonic acid salt to obtain the captioned compound 3.

$^1$H-NMR (ppm) (300 MHz, CDCl$_3$)
0.12 (2H, m), 0.52 (2H, m), 0.84 (1H, m), 1.43 (3H, m), 1.65 (1H, m), 1.76 (4H, br), 2.12 (3H, td, J=12.0, 3.6 Hz), 2.26-2.38 (7H, m), 2.63 (3H, m), 3.03 (1H, d, J=18.4 Hz), 3.08 (1H, d, J=5.6 Hz), 3.83 (1H, ddd, J=13.2, 8.4, 3.6 Hz), 5.05 (1H, d, J=8.4 Hz), 6.60 (1H, d, J=8.4 Hz) (free form)
Mass (ESI): 477 (M$^+$+1)

Reference Example 4

Synthesis of [N-(17-cyclopropylmethyl)-4,5α-epoxy-3,14-dihydroxy-morphinan-6β-yl]-O-sulfonebenzimide tartaric acid salt (Compound 4)

4

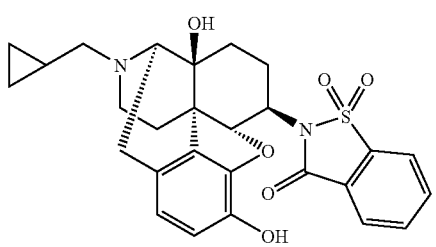

In 10 mL of chloroform, 203 mg (0.53 mmol) of 6β-amino-(17-cyclopropylmethyl)-4,5α-epoxy-3-methoxymethoxy-morphinan-14-ol was dissolved, and 0.15 mL of triethylamine and 136 mg of methyl-(2-chlorosulfonyl)-benzoate were added at 0° C., followed by stirring the mixture at room temperature for 8 hours, and then the mixture was heated to reflux for 30 minutes. After allowing the reaction solution to cool to room temperature, saturated aqueous sodium hydrogen carbonate solution was added and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 219 mg (yield: 71%) of 2-[(17-cyclopropylmethyl-4,5α-epoxy-14-hydroxy-3-methoxymethoxy-morphinan-6β-yl)-sulfamoyl]-benzoic acid methyl ester.

In 10 mL of DMF, 91 mg (0.16 mmol) of the obtained 2-[(17-cyclopropylmethyl-4,5α-epoxy-14-hydroxy-3-methoxymethoxy-morphinan-6β-yl)-sulfamoyl]-benzoic acid methyl ester was dissolved, and 352 mg of potassium carbonate was added, followed by stirring the mixture at 80° C. for 3 hours. After allowing the reaction solution to cool to room temperature, the solution was filtered through celite (trademark) and the filtrate was concentrated to obtain N-[(17-cyclopropylmethyl)-4,5α-epoxy-14-hydroxy-3-methoxymethoxy-morphinan-6β-yl]-O-sulfonebenzimide as a crude product.

In 2 mL of 2-propanol and 2 mL of chloroform, the obtained crude product was dissolved and 0.2 mL of concentrated hydrochloric acid was added, followed by stirring the mixture at room temperature for 13 hours. Saturated aqueous sodium hydrogen carbonate solution was added and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 67 mg (yield 85%: 2 steps) of free form of captioned compound 4. This product was converted to tartaric acid salt to obtain the captioned compound 4.

$^1$H-NMR (ppm) (300 MHz, CDCl$_3$)
8.06-8.08 (m, 1H), 7.82-7.97 (m, 3H), 6.80 (d, 1H, J=8.1 Hz), 6.65 (d, 1H, J=8.1 Hz), 5.28 (d, 1H, J=8.3 Hz), 3.92 (ddd, 1H, J=3.9, 8.3, 13.1 Hz), 3.11 (d, 1H, J=5.6 Hz), 3.06 (d, 1H, J=18.3 Hz), 2.78-2.87 (m, 1H), 2.60-2.70 (m, 2H), 2.32-2.39 (m, 3H), 2.13-2.20 (m, 1H), 1.46-1.76 (m, 4H), 0.82-0.88 (m, 1H), 0.52-0.57 (m, 2H), 0.12-0.15 (m, 2H) (free form)
Mass (ESI): 509 (M$^+$+1)

Reference Example 5

Synthesis of 2-[(17-cyclopropylmethyl)-4,5α-epoxy-3,14-dihydroxy-morphinan-6β-yl]-2,3-dihydro-isoindole-1-one tartaric acid salt (Compound 5)

5

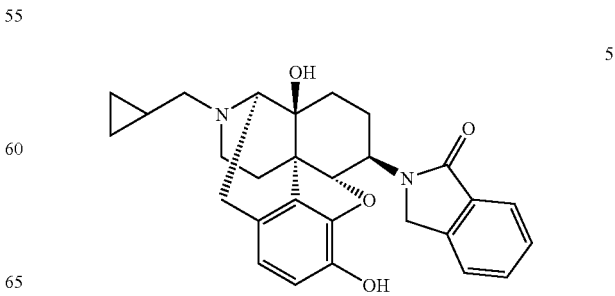

In a mixed solution of 5 mL of methanol and 5 mL of chloroform, 156 mg (0.33 mmol) of N-[(17-cyclopropylmethyl)-4,5α-epoxy-3,14-dihydroxy-morphinan-6β-yl]-phthalimide obtained in Reference Example 1 was dissolved, and 61 mg (1.61 mmol) of sodium borohydride was added at 0° C., followed by stirring the mixture for 2 hours. Thereafter, saturated aqueous sodium hydrogen carbonate solution was added and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 130 mg (yield 83%) of 2-[(17-cyclopropylmethyl)-4,5α-epoxy-3,14-dihydroxy-morphinan-6β-yl]-3-hydroxy-2,3-dihydro-isoindole-1-one (diastereomer mixture).

In a mixed solution of 7 mL of methylene chloride and 25 mL of chloroform, 150 mg (0.32 mmol) of the obtained purified product was dissolved, 0.22 mL (1.73 mmol) of boron trifluoride ether complex and 0.28 mL (1.73 mmol) of triethylsilane were added at 0° C., followed by stirring the mixture for 22 hours. Thereafter, saturated aqueous sodium hydrogen carbonate solution was added and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 55 mg (yield 38%) of free form of captioned compound 5. This product was converted to tartaric acid salt to obtain the captioned compound 5.

$^1$H-NMR (ppm) (300 MHz, CDCl$_3$)

7.85 (d, J=8.2 Hz, 1H), 7.58-7.45 (m, 3H), 6.79 (d, J=8.2 Hz, 1H), 6.62 (d, J=8.2 Hz, 1H), 4.68 (d, J=8.2 Hz, 1H), 4.52 (d, J=16.8 Hz, 1H), 4.44 (d, J=16.8 Hz, 1H), 4.27 (ddd, J=12.6, 8.2, 4.4 Hz, 1H), 3.11 (d, J=5.5 Hz, 1H), 3.06 (d, J=18.4 Hz, 1H), 2.70-2.59 (m, 2H), 2.39 (d, J=6.6 Hz, 2H), 2.31-2.12 (m, 3H), 1.72-1.49 (m, 4H), 0.93-0.79 (m, 1H), 0.58-0.50 (m, 2H), 0.17-0.11 (m, 2H) (free form)

IR (cm$^{-1}$) (KBr)

3075, 3004, 2925, 2818, 1658, 1622, 1498, 1455, 1377, 1330, 1307, 1279, 1228, 1188, 1153, 1117, 1069, 1051, 1034, 981, 943, 919, 884, 859, 740

Mass (EI): 458 (M$^+$)

Reference Example 6

Synthesis of 17-cyclopropylmethyl-4,5α-epoxy-3,14-dihydroxy-6β-(N-methylbenzamido)-morphinan hydrochloric acid salt (Compound 7)

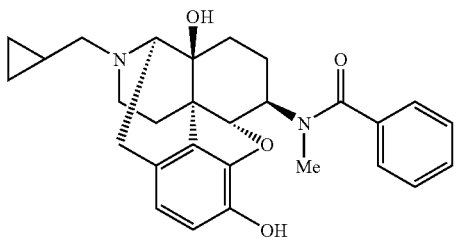

In 5 mL of chloroform, 194 mg (0.54 mmol) of 17-cyclopropylmethyl-4,5α-epoxy-3,14-dihydroxy-6β-methylamino-morphinan was dissolved, and 0.16 mL (1.11 mmol) of triethylamine and 0.13 mL (1.09 mmol) of benzoyl chloride were added, followed by stirring the mixture at room temperature for 1 hour. Then 5 mL of methanol and 1.5 mL of 2N aqueous NaOH solution were added to the reaction solution, followed by stirring the mixture at room temperature for 3 hours. Thereafter, water was added and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 237 mg (yield 95%) of free form of the captioned compound 7. This product was converted to hydrochloric acid salt to obtain the captioned compound 7.

$^1$H-NMR (ppm) (400 MHz, DMSO-d6)

7.4-7.2 (m, 5H), 6.65 (d, J=8.1 Hz, 1H), 6.50 (d, J=8.1 Hz, 1H), 4.94 (d, J=8.0 Hz, 1H), 3.74 (m, 1H), 3.3-3.1 (m, 2H), 3.03 (s, 3H), 3.0-2.8 (m, 4H), 2.5-2.3 (m, 1H), 2.2-2.1 (m, 1H), 1.65-1.55 (m, 1H), 1.45-1.35 (m, 2H), 1.3-1.2 (m, 1H), 1.1-0.9 (m, 2H), 0.7-0.3 (m, 4H)

Mass (ESI): 461 (M+1$^+$)

Example 1

Inhibitory Effect of Scratching Behavior Induced by Substance-P

Male ddY mice were purchased when they were 4 weeks old, and used in the experiments when they became 5 weeks old after acclimation. One day before experiment, each mouse had hair on the rostral back skin clipped with a hair clipper. Each of test drugs was dissolved in 10% DMSO. Either the test drug or vehicle was administered subcutaneously into the rostral back of the mouse, and 30 minutes later, Substance-P (250 nmom/site) dissolved in PBS (phosphate buffered saline) was administered intradermally into the hair-clipped skin at a dose of about 50 μL. Immediately thereafter, each mouse was put into a cage for observation (10*14*22 cm), and the subsequent behavior of each mouse was recorded by an unattended video camera for 30 minutes. The video tape was replayed, and the number of times that the mouse scratched at or around the Substance-P-administered site with its hind limb was counted. In the experiment, each group consisted of 8 mice. In cases where there was a statistically significant difference in the mean number of scratching between the solvent-administered group and the test drug-administered group, the test drug was judged to have an antipruritic effect. The results are shown in terms of the predicted administration dosage at which the number of scratching was reduced to half of that in the solvent-administered group (Table 5).

TABLE 5

| Compound | ED50 (mg/kg, sc) |
|---|---|
| 1 | 0.0034 |
| 2 | 0.32 |
| 3 | 0.0033 |
| 4 | 0.0081 |
| 5 | 0.015 |
| 6 | 0.0029 |
| 7 | 0.55(Reference Example) |

INDUSTRIAL AVAILABILITY

Since the antipruritic has an excellent antipruritic effect and has small side effects, it is useful for treatment of pruritus accompanying various diseases.

The invention claimed is:

1. A method of inhibiting or reducing occurrence or intensity of pruritus comprising administering to a patient an effective amount of one or more of said morphinan derivative having a nitrogen-containing cyclic group of the Formula (Ia):

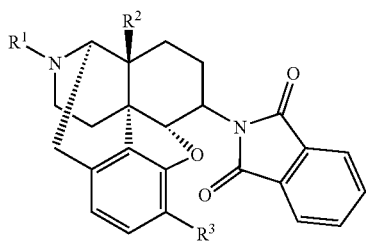 (Ia)
wherein R[1] is cyclopropylmethyl;
R[2] and R[3] are independently hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy;
and the Formula (Ia) includes (+), (−) and (±) isomers or the pharmaceutically acceptable acid addition salt thereof.
2. The method according to claim 1, wherein in said Formula (Ia), R[2] and R[3] are hydroxy.
* * * * *